United States Patent
Sato et al.

(10) Patent No.: US 10,132,899 B2
(45) Date of Patent: Nov. 20, 2018

(54) MAGNETIC RESONANCE IMAGING APPARATUS WITH VOXEL SIZE CONTROL BASED ON IMAGING PARAMETERS AND MAGNETIC SUSCEPTIBILITY

(71) Applicant: Hitachi, Ltd., Tokyo (JP)

(72) Inventors: Ryota Sato, Tokyo (JP); Toru Shirai, Tokyo (JP); Yo Taniguchi, Tokyo (JP); Yoshihisa Soutome, Tokyo (JP); Yoshitaka Bito, Tokyo (JP)

(73) Assignee: HITACHI, LTD., Tokyo (JP)

( * ) Notice: Subject to any disclaimer, the term of this patent is extended or adjusted under 35 U.S.C. 154(b) by 970 days.

(21) Appl. No.: 14/406,088

(22) PCT Filed: Jun. 24, 2013

(86) PCT No.: PCT/JP2013/067290
§ 371 (c)(1),
(2) Date: Dec. 5, 2014

(87) PCT Pub. No.: WO2014/057716
PCT Pub. Date: Apr. 17, 2014

(65) Prior Publication Data
US 2015/0168525 A1    Jun. 18, 2015

(30) Foreign Application Priority Data
Oct. 10, 2012  (JP) ................. 2012-224687

(51) Int. Cl.
*A61B 5/055*   (2006.01)
*G01R 33/56*   (2006.01)
*G01R 33/54*   (2006.01)

(52) U.S. Cl.
CPC ....... *G01R 33/5608* (2013.01); *G01R 33/543* (2013.01); *G01R 33/546* (2013.01); *A61B 5/055* (2013.01)

(58) Field of Classification Search
USPC ................. 324/300–322; 600/407–435; 382/128–131
See application file for complete search history.

(56) References Cited

U.S. PATENT DOCUMENTS 5,544,653 A * 8/1996 Takahashi .......... G01R 33/4835
                                                       324/309
6,687,527 B1    2/2004 Wu et al.
(Continued)

FOREIGN PATENT DOCUMENTS

JP    8-336504 A    12/1996
JP    2002-511330 A    4/2002
(Continued)

OTHER PUBLICATIONS

E. M. Haacke, et al, "Susceptibility Mapping as a Means to Visualize Veins and Quantify Oxygen Saturation", Journal of Magnetic Resonance Imaging 32:663-373, 2010, Wiley-Liss, Inc.
(Continued)

*Primary Examiner* — Melissa Koval
*Assistant Examiner* — Tiffany Fetzner
(74) *Attorney, Agent, or Firm* — Brundidge & Stanger, P.C.

(57) ABSTRACT

A magnetic resonance imaging apparatus comprising a measurement parameter-setting unit for setting measurement parameters that determine the strength and timing of the high frequency magnetic field and the gradient magnetic field, and a measuring unit for applying the high frequency magnetic field and the gradient magnetic field on a subject placed in the static magnetic field according to the measurement parameters and detecting the nuclear magnetic resonance signal generated from the subject as a complex signal. The measurement parameter-setting unit is equipped with: a basic parameter-inputting section for setting the imaging parameters and imaging cross-section; a limiting condition-
(Continued)

inputting section for setting limiting conditions that apply limits on the setting of the voxel size; a voxel size-calculating section for setting the voxel size according to the limiting conditions; and a voxel size-displaying section for displaying the set voxel size to the user.

14 Claims, 18 Drawing Sheets

(56) References Cited

U.S. PATENT DOCUMENTS

| | | | | |
|---|---|---|---|---|
| 7,692,424 B2* | 4/2010 | Cheng | ............ | G01R 33/56 324/309 |
| 8,886,283 B1* | 11/2014 | Chen | ............ | A61B 5/055 382/128 |
| 9,213,076 B2* | 12/2015 | Liu | ............ | G01R 33/56545 |
| 9,766,316 B2* | 9/2017 | Sato | ............ | G01R 33/5608 |
| 2002/0087066 A1 | 7/2002 | Hellinger | | |
| 2003/0212322 A1* | 11/2003 | Haacke | ............ | G01R 33/56 600/410 |
| 2004/0102691 A1* | 5/2004 | Mallozzi | ............ | G01R 33/565 600/410 |
| 2009/0219023 A1* | 9/2009 | Cheng | ............ | G01R 33/56 324/312 |
| 2010/0052676 A1 | 3/2010 | Sugiura | | |
| 2013/0221961 A1* | 8/2013 | Liu | ............ | G01R 33/56545 324/307 |
| 2015/0168525 A1* | 6/2015 | Sato | ............ | G01R 33/543 324/318 |
| 2015/0338492 A1* | 11/2015 | Sato | ............ | G01R 33/5608 600/410 |

FOREIGN PATENT DOCUMENTS

| | | |
|---|---|---|
| JP | 2002-191577 A | 7/2002 |
| JP | 2005-501624 A | 1/2005 |
| JP | 2008-093276 A | 4/2008 |
| JP | 2010-005064 A | 1/2010 |
| JP | 2010-051391 A | 3/2010 |

OTHER PUBLICATIONS

Tian Liu, et al, "Cerebral Microbleeds: Burden Assessment by Using Quantify Susceptibility Mapping", Radiology: vol. 262: No. 1, Jan. 2012, pp. 269-278.

International Search Report from International Application No. PCT/JP13/067290 dated Aug. 13, 2013.

* cited by examiner

FIG. 11

| RECOMMENDED PARAMETER | | 710 |
|---|---|---|
| NUMBER OF LEAD-OUT ENCODINGS | | 512 |
| NUMBER OF PHASE ENCODINGS | | 256 |
| SLICE THICKNESS | | 1 |
| PHASE ENCODING DIRECTION | | HF |

| | | 720 |
|---|---|---|
| SNR | | 100 |
| IN-PLANE RESOLUTION | | 0.5 |
| IMAGING TIME | | 8:12 |

MAGNETIC RESONANCE IMAGING APPARATUS WITH VOXEL SIZE CONTROL BASED ON IMAGING PARAMETERS AND MAGNETIC SUSCEPTIBILITY

TECHNICAL FIELD

The present invention relates to a magnetic resonance imaging (MRI) technology, and more particularly, to the technology for supporting measurement parameter setting in generation of a magnetic susceptibility image.

BACKGROUND

The magnetic resonance imaging (MRI) apparatus is a medical image diagnosis apparatus configured to apply high frequency magnetic field and gradient magnetic field to a subject placed in the static magnetic field so that the signal generated from the subject is measured and imaged through nuclear magnetic resonance. The MRI apparatus mainly has two types, that is, tunnel type of a horizontal magnetic field, and open type of a vertical magnetic field. The MRI apparatus of former type applies the static magnetic field in the direction parallel to the subject's body axis, and MRI apparatus of latter type applies the static magnetic field in the direction vertical to the subject's body axis.

The MRI apparatus is configured to allow acquisition of the image in an arbitrary imaging cross-section. The imaging cross-section includes three cross-sections orthogonal to one another, that is, a transverse section for separating the body into a head side and a foot side, a coronary section for separating the body into a ventral side and a dorsal side, and a sagittal section for separating the body into a left side and a right side as well as an oblique section for obliquely separating the body at an arbitrary angle.

Generally, the MRI apparatus is configured to apply a slice gradient magnetic field for specifying the imaging cross-section, and simultaneously to give an excitation pulse (high frequency magnetic field pulse) for exciting the in-plane magnetization so as to obtain the nuclear magnetic resonance signal (echo) generated at the stage where the excited magnetization converges. At this time, the apparatus further applies the phase encoding gradient magnetic field and the lead-out gradient magnetic field in the direction vertical to the slice gradient magnetic field with respect to the imaging cross-section within the period from the excitation to acquisition of the echo for the purpose of imparting the three-dimensional positional information to magnetization. The measured echo is placed in the space k with axes of kx, ky and kz, which is subjected to the image reconstruction through inverse Fourier transformation.

Each pixel value of the reconstructed image becomes a complex number including an absolute value and a deflection angle (phase). The absolute value and the phase are determined by imaging parameters including the static magnetic field intensity, the static magnetic field direction, type of the imaging sequence, the voxel size and the repetition time, the density of magnetization in the subject and relaxation times (T1, T2).

Normal diagnosis uses the grayscale image (magnitude image), taking the absolute value as the pixel value. The magnitude image is excellent in visualization of the tissue structure, and includes various kinds of images, for example, a proton (hydrogen nucleus) density high-contrast image, a T1 high-contrast image, a T2 high-contrast image, a diffusion high-contrast image, and a vascular image. Meanwhile, the grayscale image (phase image) taking the phase as the pixel value reflects change in the magnetic field resulting from uneven static magnetic field, and difference in the magnetic susceptibility among biotissues. The phase image has been used for adjustment of measurement parameters more often than the use for the diagnosis.

Recently, the use of the phase image that reflects the change in the magnetic field resulting from the magnetic susceptibility difference has been positively applied to the study on estimation of the magnetic susceptibility distribution in vivo from the phase image so that the estimated magnetic susceptibility distribution is used for the image diagnosis. In the brain, for example, the ratio of the paramagnetic substance content differs dependent on the respective tissues. The vein and bleeding part each containing large quantity of deoxyhemoglobin as the paramagnetic substance exhibit higher magnetic susceptibility compared with the surrounding tissue. Therefore, imaging of the magnetic susceptibility distribution in vivo allows imaging of the vein distribution (see Haacke E M, et al., Susceptibility mapping as a means to visualize veins and quantify oxygen saturation, Journal of Magnetic Resonance Imaging vol. 32, pp. 663-676 (2010)), and detection of the microbleed (see Liu T, et al., Cerebral Microbleeds: Burden assessment by using quantitative susceptibility mapping, Radiology, vol. 262, no. 1, pp. 269-278 (2012)).

SUMMARY

The tissue smaller than the voxel, for example, vein and microbleed has a problem that the magnetic susceptibility estimation accuracy changes depending on the voxel size to deteriorate the contrast of the tissue on the estimated magnetic susceptibility image. This is thought to be caused by the partial volume effect of the phase image. The phase distribution of the phase image that is equal to or smaller than the voxel size will be averaged within the voxel by the partial volume effect. Then the tissue smaller than the voxel has the phase accuracy deteriorated to change the phase image contrast. Accordingly, change in the voxel size of the phase image will vary the magnetic susceptibility estimation accuracy estimated from the phase image.

Due to the aforementioned reason, it is necessary to set the voxel size which allows the magnetic susceptibility estimation with high accuracy for the purpose of visualizing the image of the vein and microbleed with high accuracy. However, as the phase distribution varies with the static magnetic field direction to the imaging cross-section and the shape of the target tissue, the partial volume effect of the phase image will vary with the static magnetic field direction to the imaging cross-section and the shape of the target tissue. As a result, it is necessary to consider the influence of those two factors when setting the voxel size which allows the magnetic susceptibility estimation with high accuracy. The voxel size influences not only the magnetic susceptibility estimation accuracy but also the imaging conditions such as an SNR (Signal-to-Noise Ratio) of the image, the in-plane resolution of the imaging cross-section, and the imaging time. The allowable range of the imaging condition may vary depending on the apparatus and the user. It is therefore necessary to set the voxel size in the range limited by those imaging conditions.

The present invention has been made in view of the above circumstances, and it is an object of the present invention to provide the technology enabling the magnetic susceptibility estimation of the target tissue with high accuracy by calculating the appropriate voxel size in accordance with the static magnetic field direction with respect to the imaging cross-section, the target tissue, and the imaging condition.

The present invention is configured to calculate the voxel size enabling to estimate the magnetic susceptibility with high accuracy in accordance with the set parameter and the condition including the imaging parameter, imaging cross-section, target tissue, and imaging condition, and generate the magnetic susceptibility image from the magnitude image and the phase image measured in accordance with the calculated voxel size.

Specifically, the magnetic resonance imaging apparatus is provided with a static magnetic field application unit for applying a static magnetic field to a subject, a gradient magnetic field application unit for applying a gradient magnetic field to the subject, a high frequency magnetic field pulse irradiation unit for irradiating the subject with a high frequency magnetic field pulse, a receiving unit for receiving a nuclear magnetic resonance signal from the subject, and a calculation unit for performing an operation with respect to the received nuclear magnetic resonance signal by controlling the gradient magnetic field and the high frequency magnetic field pulse. The calculation unit includes a measurement parameter setting unit that sets a measurement parameter which determines intensity and timing of a high frequency magnetic field and the gradient magnetic field, a measuring unit that applies the high frequency magnetic field and the gradient magnetic field to the subject placed in the static magnetic field in accordance with the measurement parameter to detect the nuclear magnetic resonance signal generated from the subject as a complex signal, an operation unit that performs an operation with respect to the complex signal to generate an image, and a display processing unit that displays the generated image on a display device. The measurement parameter setting unit includes a basic parameter inputting unit that sets an imaging parameter and an imaging cross-section, a limiting condition inputting unit that sets a limiting condition for limiting a voxel size setting, a voxel size calculating unit that sets the voxel size in accordance with the limiting condition, and a voxel size displaying unit that displays the set voxel size to a user.

The present invention ensures estimation of the magnetic susceptibility of the target tissue with high accuracy by calculating the appropriate voxel size in accordance with the static magnetic field direction with respect to the imaging cross-section, the target tissue and the imaging condition.

BRIEF DESCRIPTION OF THE DRAWINGS

FIG. 11 is an exemplary screen according to the embodiment, displaying the calculated voxel size to the user.

DESCRIPTION OF A PREFERRED EMBODIMENT

Figure 1A:
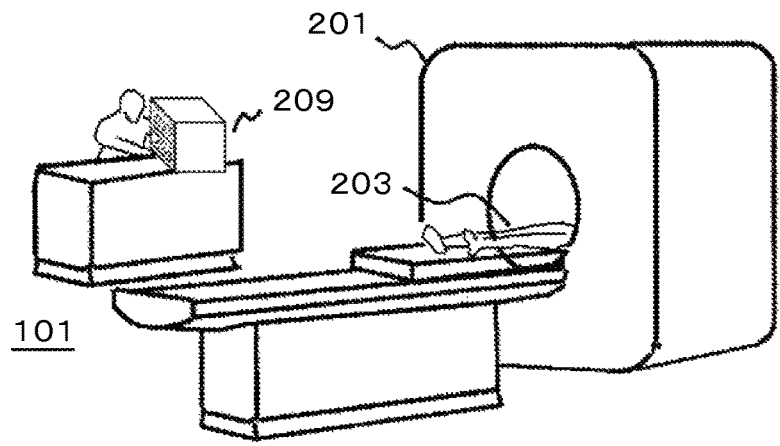
FIG. 1A is an outline view of an MRI apparatus of horizontal magnetic field type as a representative embodiment of the present invention.

An embodiment to which the present invention is applied will be described referring to the drawings. In the entire drawings, the element with the same function will be designated with the same code, and explanation thereof, thus will be omitted. It is to be understood that the following explanations are not intended to limit the present invention.

Figure 1B:
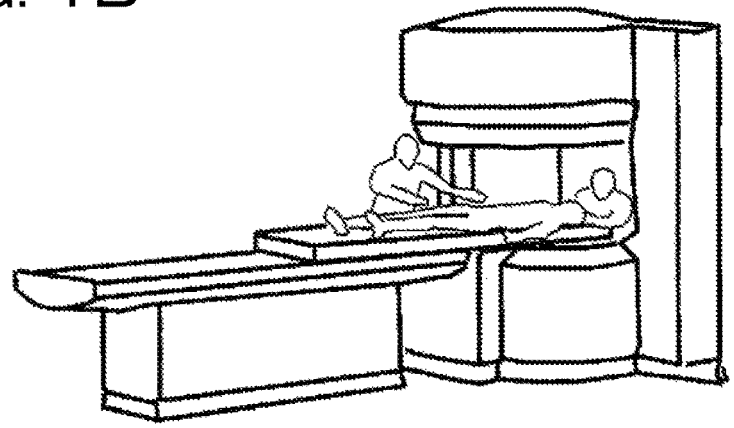
FIG. 1B is an outline view of the MRI apparatus of vertical magnetic field type as another embodiment.
Figure 1C:
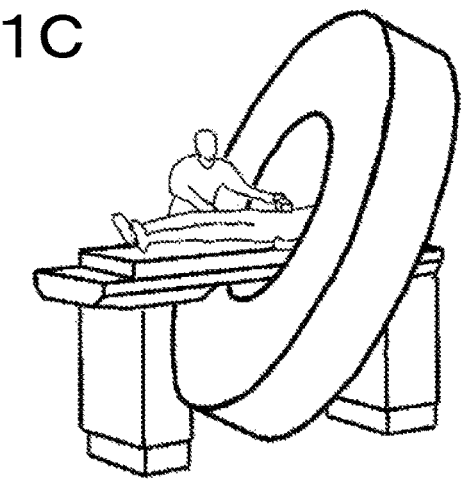
FIG. 1C is an outline view of the MRI apparatus with improved open feel as another embodiment.

FIG. 1A is an outline view of an MRI apparatus as a representative embodiment of the present invention. An MRI apparatus 101 includes a tunnel type magnet 201 that generates a static magnetic field with the solenoid coil so that a subject 203 who lies down on a bed is moved into its bore for imaging. This type of apparatus is called the MRI apparatus of horizontal magnetic field type. An object of the present invention is to estimate the magnetic susceptibility of the target tissue with high accuracy irrespective of the static magnetic field direction of the MRI apparatus, which is applicable to any type of the MRI apparatus besides the horizontal magnetic field type as described above. FIG. 1B shows the MRI apparatus of another type, that is, the MRI apparatus of vertical magnetic field type, which employs upper and lower separated magnets. FIG. 1C shows the MRI apparatus of still another type using the obliquely tilted tunnel type magnet with shortened depth for the improved open feel.

The embodiment employs the coordinate system, setting the static magnetic field direction of the MRI apparatus 101 to the z-direction, one of the two vertical directions, which is in parallel with the bed surface on which the subject to be measured lies down to the x-direction, the other direction vertical to the bed surface to the y-direction. The static magnetic field will be simply referred to as the magnetic field.

Figure 2:
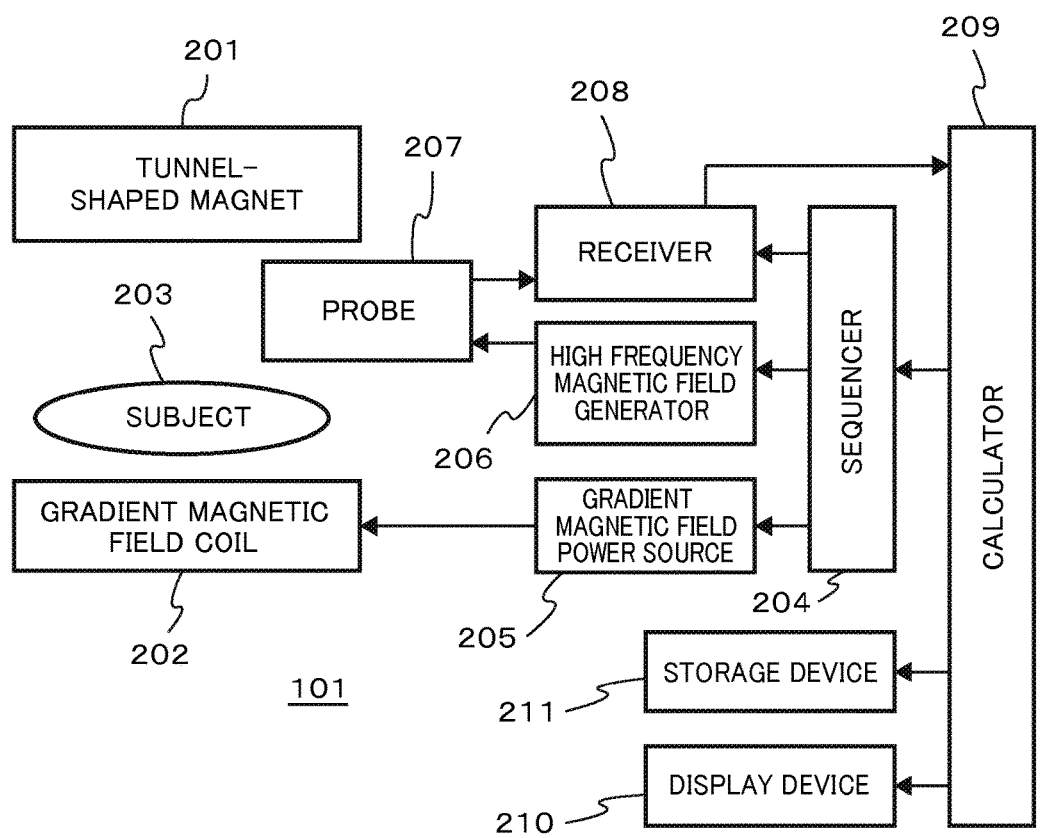
FIG. 2 is a block diagram schematically showing a structure of the MRI apparatus according to the embodiment.
Figure 3:
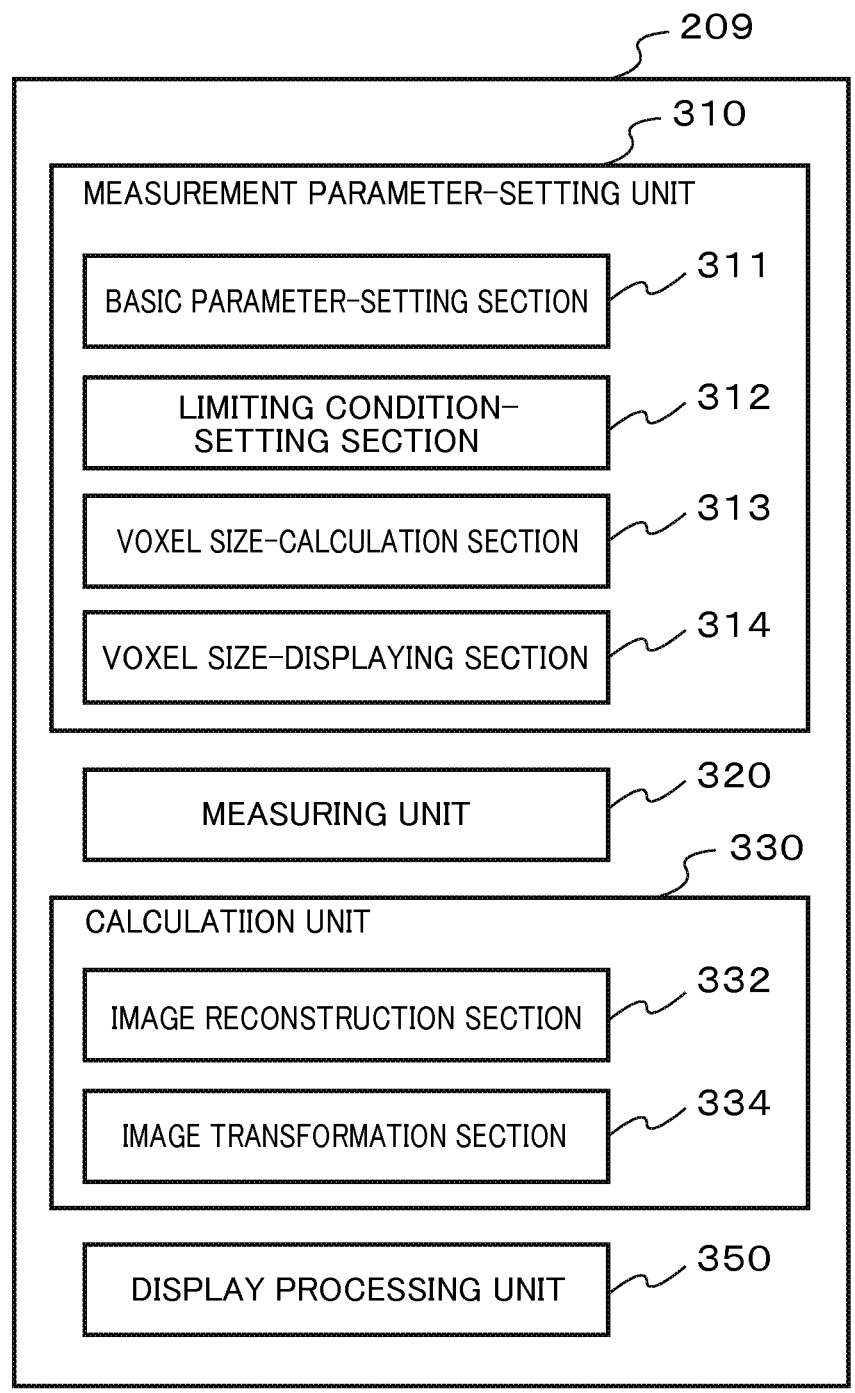
FIG. 3 is a function block diagram of a calculator of the embodiment.

FIG. 2 is a block diagram schematically showing a structure of the MRI apparatus 101 of the embodiment. The MRI apparatus 101 includes the tunnel type magnet 201 that generates the static magnetic field in the direction parallel to the subject, a gradient magnetic field coil 202 that generates the gradient magnetic field, a sequencer 204, a gradient magnetic field power source 205, a high frequency magnetic field generator 206, a probe 207 that irradiates the high frequency magnetic field and detects the nuclear magnetic resonance signal (echo), a receiver 208, a calculator 209, a display device 210, and a storage device 211.

The sequencer 204 sends a command to the gradient magnetic field power source 205 and the high frequency magnetic field generator 206 so that the gradient magnetic field and the high frequency magnetic field are generated, respectively. The generated high frequency magnetic field is applied to the subject 203 through the probe 207. The echo generated from the subject 203 is received by the probe 207, and detected by the receiver 208. The nuclear magnetic resonance frequency (detection reference frequency f0) as the reference for detection is set by the sequencer 204. The detected signal is sent to the calculator 209 so that the signal processing such as the image reconstruction is executed. The result is displayed on the display device 210. The storage device 211 may be configured to store the detected signal, measurement conditions, and the image information after processing the signal as needed. The sequencer 204 controls so that the respective components are operated with preliminarily programmed intensity at the preliminarily programmed timing. Descriptions on the high frequency magnetic field, gradient magnetic field, timing and intensity of the signal reception among the programs are called pulse sequence. Various types of pulse sequence in accordance with the object have been known. The MRI apparatus 101 according to the embodiment employs the pulse sequence of GrE (Gradient Echo) system which provides the signal corresponding to the nonuniformity of the spatial distribution of the magnetic field intensity. The pulse sequence of GrE system includes, for example, RSSG (RF-Spoiled-Steady-State Acquisition with Rewound Gradient-Echo) sequence.

The calculator 209 according to the embodiment activates the respective components of the MRI apparatus 101 in accordance with the pulse sequence to measure the echo, and executes various calculations (to be described later) of the measured echo to acquire an image with the required contrast.

For the purpose of realizing the aforementioned function, the calculator 209 of the embodiment includes a measurement parameter setting unit 310 for setting the measurement parameter, a measuring unit 320 that instructs the sequencer 204 to measure the echo in accordance with the set measurement parameter to place the acquired echo in the space k, a calculation unit 330 that executes calculation with respect to the echo placed in the space k for generating the image, and a display processing unit 350 that allows the display device 210 to display the acquired image. The calculation unit includes an image reconstruction section 332 that reconstructs the complex image based on the echo placed in the space k, and an image transformation section 334 that executes a predetermined calculation with respect to the reconstructed complex image to generate the magnetic susceptibility image.

The respective functions of the calculator 209 are realized by its CPU which loads the program stored in the storage device 211 into the memory for execution.

Figure 4:
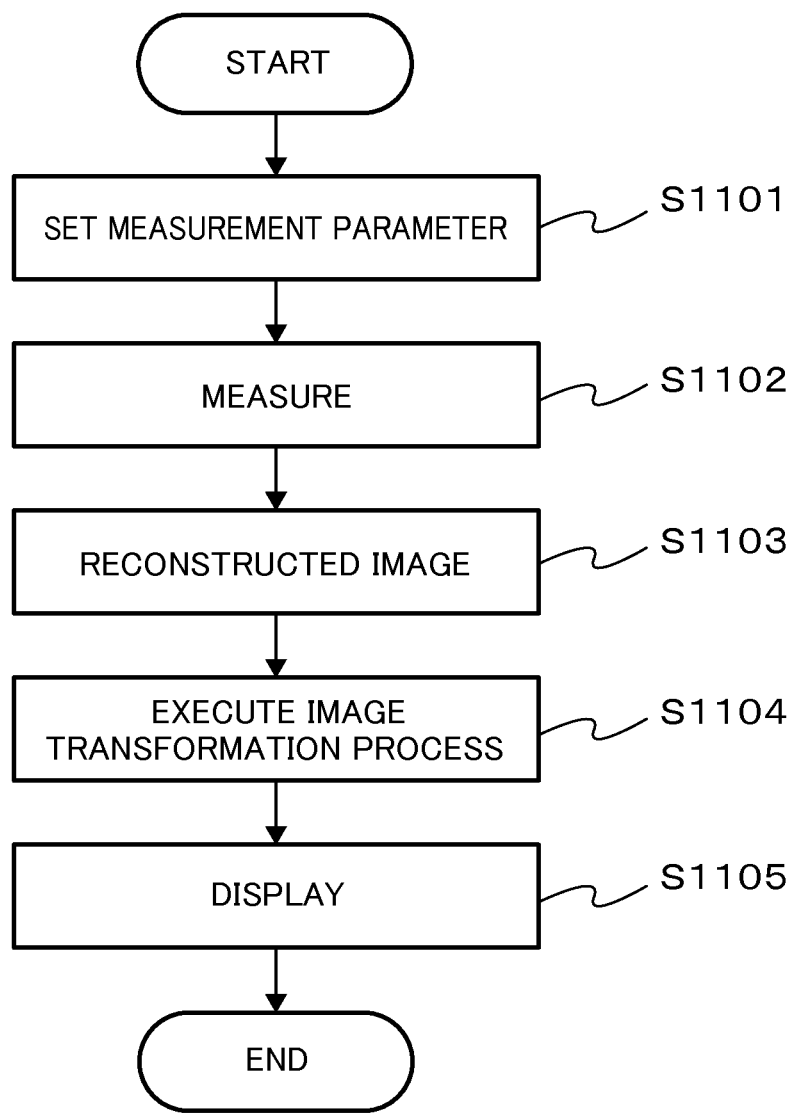
FIG. 4 is a flowchart of an imaging process according to the embodiment.

The imaging process executed by the measurement parameter-setting unit 310, the measuring unit 320, the image reconstruction section 332, the image transformation section 334, and the display processing unit 350 of the calculator 209 according to the embodiment will be described in detail along the process flow. FIG. 4 is a flowchart of the imaging process according to the embodiment.

A basic parameter-inputting section 311 sets the imaging parameters such as the pulse sequence, imaging cross-section, TR (Repetition time) and TE (Echo time). A limiting condition-inputting section 312 sets the imaging condition that limits setting of the voxel size such as the target tissue for imaging, the SNR of the image, the in-plane resolution of the imaging cross-section, and the imaging time. A voxel size-calculation section 313 calculates the voxel size based on the limiting condition set by the limiting condition-inputting section and the static magnetic field direction with respect to the imaging cross-section. A voxel size-displaying section 314 displays the calculated voxel size to the user. The aforementioned process steps correspond to step S1101 of the process flow shown in FIG. 4 for setting the measurement parameter. Thereafter, in response to the instruction for starting the measurement, the measurement is started in step 1102. The respective steps in step 1102 onwards will be described later in sequence. The detailed process executed in step 1101, that is, the process executed by the respective components of the measurement parameter-setting unit will be described in order.

Figure 5:
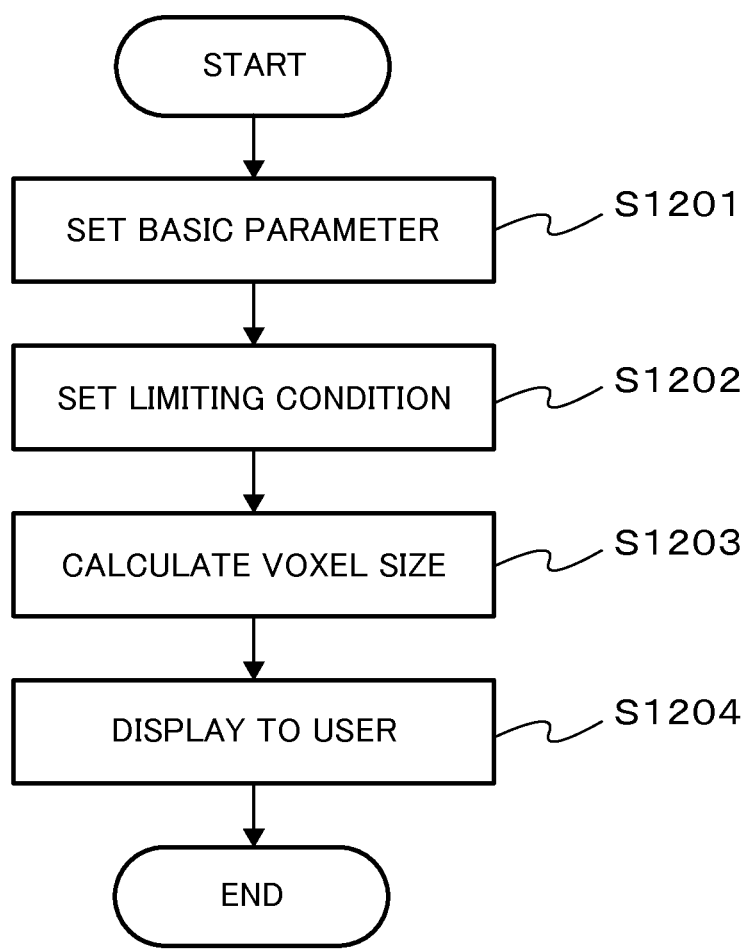
FIG. 5 is a flowchart of a measurement parameter setting process according to the embodiment.

FIG. 5 is a flowchart of the process executed by the measurement parameter-setting unit. The basic parameter-inputting section 311 allows the user to set the pulse sequence, the imaging cross-section and the imaging parameter via the display device 210. In the embodiment, the pulse sequence is set to RSSG, the imaging cross-section is of coronary type, the imaging parameter is set to have TR=60 ms, TE=40 ms, FA (Flip Angle)=25°, NSA (Number of Signals Averaged: number of integrations)=1, visual field in the imaging cross-section=256 mm×256 mm, and visual field in the slice direction=32 mm. Arbitrary values may be used for setting the pulse sequence, imaging cross-section and imaging parameter.

Figure 6:
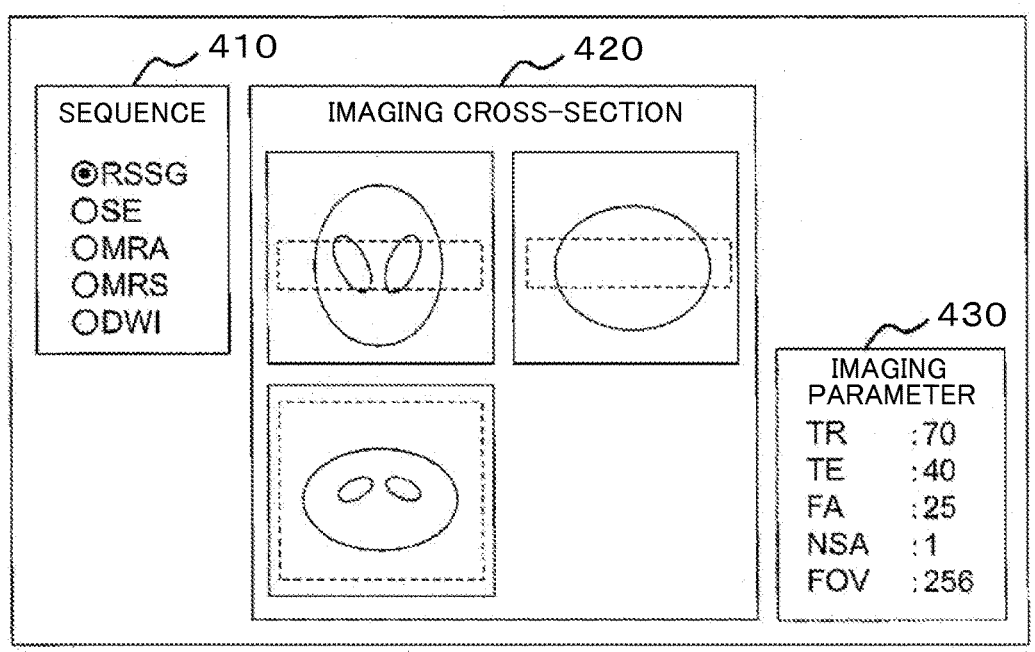
FIG. 6 is a view representing an exemplary parameter setting screen for a basic parameter setting process according to the embodiment.

FIG. 6 shows an example of a parameter setting screen. A pulse sequence-setting section 410 sets the pulse sequence, and an imaging cross-section setting section 420 sets the imaging cross-section. An imaging parameter-setting section 430 sets the imaging parameter. FIG. 6 shows an example of the parameter setting screen, which is not limited thereto.

Then the limiting condition-inputting section 312 sets the target tissue, the SNR which can be imaged, the in-plane resolution and the imaging time range.

In this embodiment, the SNR is defined by the rate of change (%) from the reference value, and the in-plane resolution is defined by the area (mm$^2$) of 1 pixel in the imaging cross-section, and each resolution (mm) in two directions of the in-plane cross-section. The reference value of the SNR is set to 100% when setting the voxel size (dx (resolution in x-direction)=0.5 mm, dy (resolution in y-direction)=2 mm, dz (resolution in z-direction)=0.5 mm) normally employed for the magnetic susceptibility high-contrast image, which is mainly employed for visualizing the vein. The SNR and the in-plane resolution may be arbitrarily defined. For example, the SNR may be defined as a specific value rather than the rate of change, and the in-plane resolution may be defined only as the area of 1 pixel in the imaging cross-section.

The relationship of the SNR, in-plane resolution, imaging time with the voxel size (dX, dY, dZ) will be described. The SNR is in proportional to the voxel volume. If the voxel size is set to have dX0, dY0, dZ0 obtained when the SNR becomes the reference value of SNR0, the relationship of $SNR=SNR0 \cdot (dX \cdot dY \cdot dZ)/(dX0 \cdot dY0 \cdot dZ0)$ is established. Assuming that the slice direction is set to Y-direction, the area of 1 pixel in the imaging cross-section as the in-plane resolution becomes $dX \cdot dZ$ (mm$^2$), and each resolution in two directions of the imaging cross-section becomes dX (mm) and dY (mm), respectively. The imaging time is obtained as a product of the TR(s), the matrix size Mp in the phase encoding direction, and matrix size Ms in the slice encoding direction, and NSA. The phase encoding direction is any one of the two directions in the imaging cross-section, having smaller matrix size. The matrix sizes MX, MY, MZ are expressed as MX=FOVX/dX, MY=FOVY/dY, MZ=FOVZ/dZ, using visual fields of FOVX (mm), FOVY (mm), and FOVZ (mm) in the respective directions. Therefore, the imaging time T(s) is expressed as $T=TR \cdot \min(MX, MZ) \cdot MY \cdot NSA = TR \cdot \min(FOVX/dX, FOVZ/dZ) \cdot (FOVY/dY) \cdot NSA$ on the assumption that the slice direction is set to Y-direction.

In this embodiment, it is assumed that the vein spatially runs through the target tissue omnidirectionally. The rate of change of the SNR is set to be in the range from 95% to 105%, the upper limit of the single pixel area of the in-plane resolution is set to 0.5 mm$^2$, the lower limit of each resolution in the two directions is set to 0.5 mm, and the upper limit of the imaging time is set to 8 minutes 12 seconds. The upper limit value of the imaging time is derived from setting the aforementioned voxel size that is normally used for the magnetic susceptibility high-contrast image. The target tissue may be arbitrarily set, for example, the vein or microbleed in the specific direction. It is also possible to arbitrarily set each range of the SNR, the in-plane resolution and the imaging time. The target tissue and the imaging condition do not have to be completely set. They may be partially set. The user is allowed to have setting with the limiting condition setting screen on the display device 210, or to set the limiting condition preliminarily stored in the storage device 211. It may be configured to allow the user to set only a part of the limiting condition while setting the rest of the limiting condition stored in the storage device 211.

Figure 7:
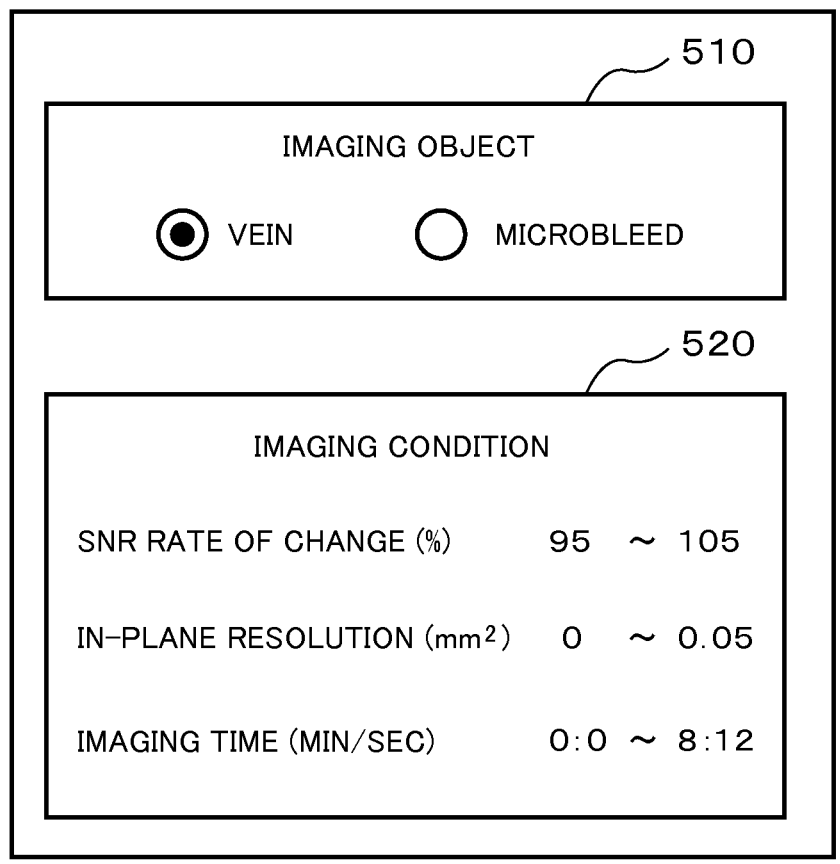
FIG. 7 is a view representing an exemplary limiting condition setting screen for a limiting condition setting process according to the embodiment.

FIG. 7 shows an example of the limiting condition-setting section of the display device 211, which is set by the user. Referring to FIG. 7, the target tissue is set on a target tissue setting section 510, and each range of the SNR rate of change (%), the in-plane resolution (mm$^2$), and the imaging time (min, sec) is determined on an imaging condition-setting section 520. FIG. 7 shows an example of the limiting condition setting screen, which is not restricted to the one shown in FIG. 7.

Figure 8:
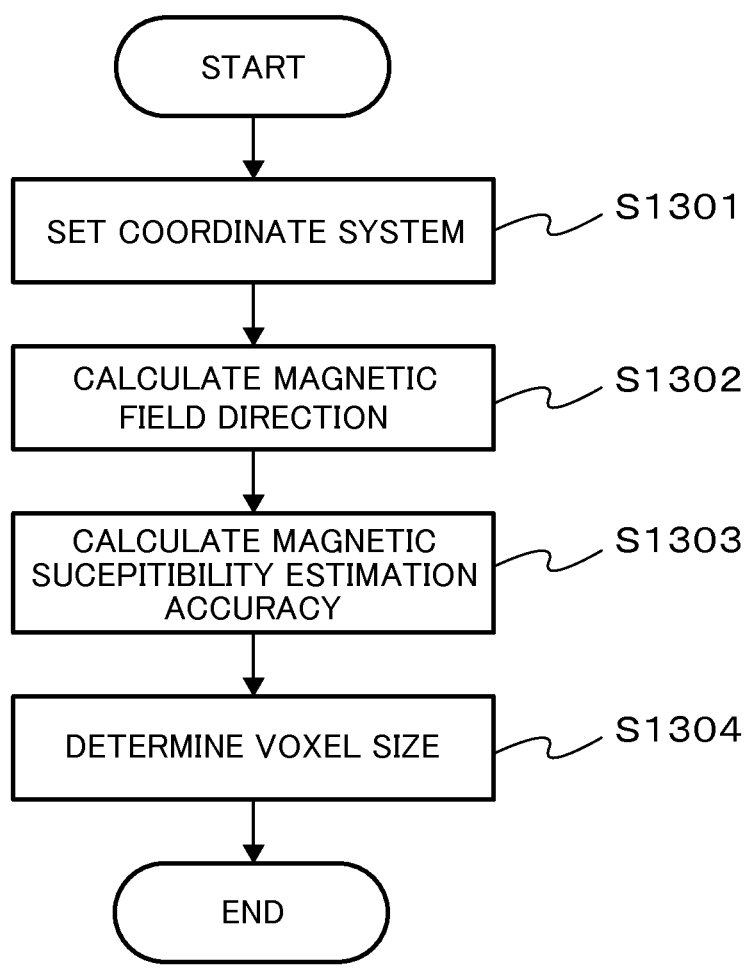
FIG. 8 is a flowchart of a voxel size calculation process according to the embodiment.

The voxel size-calculating section 313 calculates the voxel size which allows estimation of the magnetic susceptibility of the target tissue with high accuracy. The voxel size-calculating section 313 according to the embodiment primarily calculates the static magnetic field direction with respect to the imaging cross-section, and calculates the magnetic susceptibility estimation accuracy of the target tissue with respect to all the voxel sizes in the limiting condition so as to determine the optimum voxel size in accordance with the calculated magnetic susceptibility estimation accuracy. Details of the process executed by the voxel size-calculating section according to the embodiment will be explained in sequence referring to FIG. 8.

Figure 9:
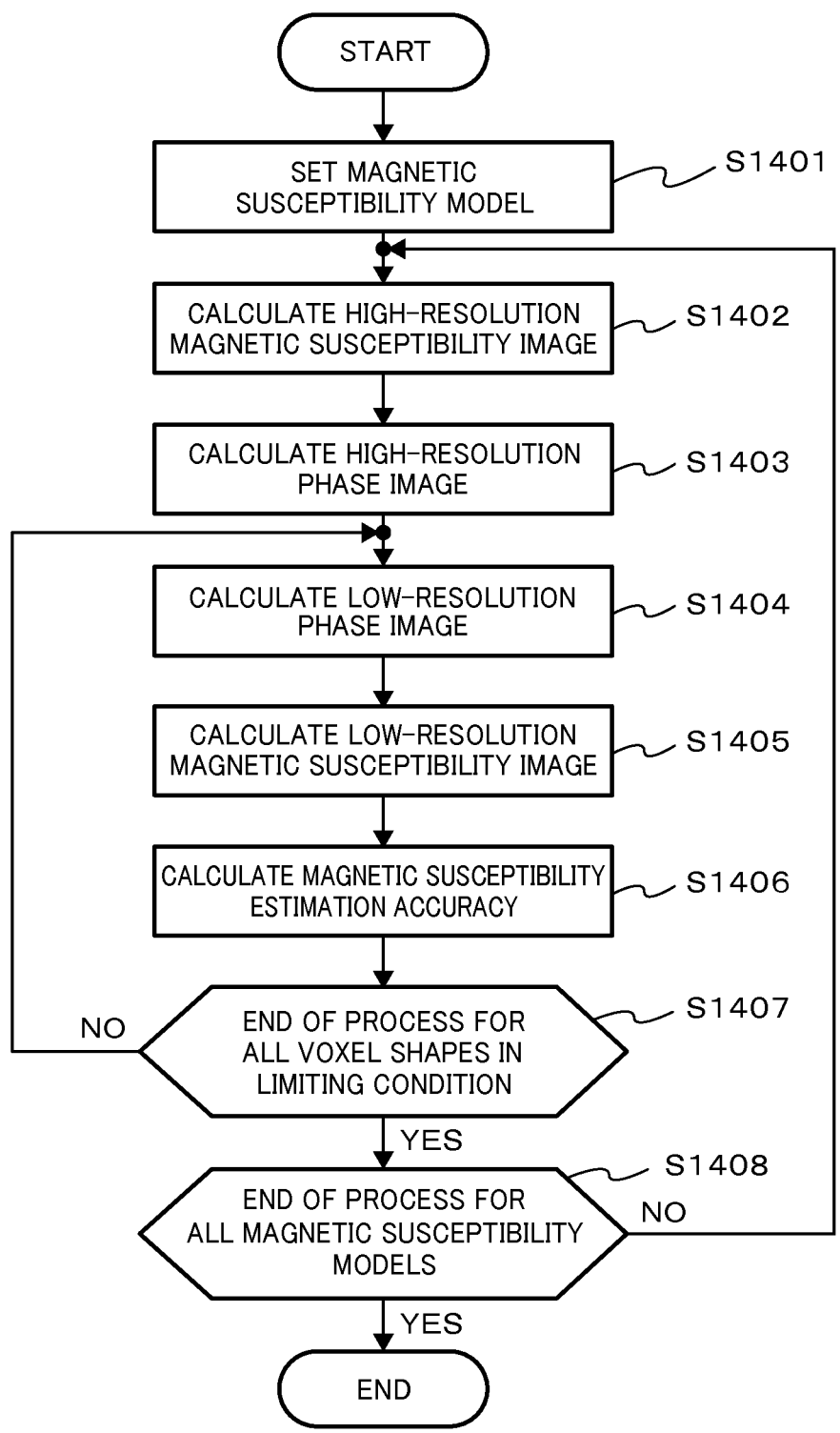
FIG. 9 is a flowchart of a magnetic susceptibility estimation accuracy calculation process according to the embodiment.

The coordinate system used by the voxel size-calculating section is set in step S1301. In this embodiment, two directions in the imaging cross-section (coronal section), that is, the RL direction (Right-Left direction of body) and the HF direction (Head-Foot direction of body) are defined as X-direction and Z-direction, respectively. The slice direction is defined as Y-direction. However, arbitrary coordinate axis may be used without being limited to the one as described above. It is necessary to set axes corresponding to three directions respectively, by which the voxel size is defined. Then the static magnetic field direction in the set coordinate system is calculated in step S1302. As this embodiment uses the MRI of horizontal magnetic field type, the Z-direction in the set coordinate system corresponds to the static magnetic field direction. Each magnetic susceptibility estimation accuracy of all the target tissues corresponding to all the voxel sizes in the limiting condition is calculated in step S1303. In this embodiment, the magnetic susceptibility estimation accuracy is calculated through calculator simulation. In order to calculate the magnetic susceptibility estimation accuracy, the magnetic susceptibility model of the target tissue is set, the high resolution magnetic susceptibility image is calculated from the magnetic susceptibility model, the high resolution phase image is calculated from the high resolution magnetic susceptibility image, the low resolution phase image is calculated from the high resolution phase image, the low resolution magnetic susceptibility image is calculated from the low resolution phase image, and the magnetic susceptibility estimation accuracy is calculated from the low resolution magnetic susceptibility image. The method of calculating the magnetic susceptibility estimation accuracy according to the embodiment will be described referring to FIG. 9.

Each magnetic susceptibility model is set for all the target tissues set through the limiting condition-inputting section in step S1401. In this embodiment, the vein spatially running omnidirectionally is set as the target tissue. The embodiment models the vein shape as a column with diameter D set to 0.5 (mm), and length L set to 10 (mm). The magnetic susceptibility value of the vein $\chi v$ is set to 0.3 (ppm), and the magnetic susceptibility value xe of the element other than the vein is set to 0 (ppm). For setting the vein running omnidirectionally, the center of the vein model is set as the origin of the coordinate, the zenith angle between the Z-direction and the vein running direction is set to θ1, and the azimuth angle between the X-direction and the vein running direction upon projection on the XY plane is set to θ2. Each angle of θ1 and θ2 is changed by 10°, respectively in the range from 0° to 90°. The vein may be modeled by any other shape besides the column. Arbitrary values may be set to define the D, L, $\chi v$, $\chi e$ without being limited to the aforementioned values. The running direction may also be set by the arbitrary method. If the tissue other than the vein is set as the target tissue, it may be modeled into the shape suitable for the respective tissues. For example, if the microbleed is defined as the target tissue, it may be modeled into the spherical shape.

Then the magnetic susceptibility image with high resolution is generated from the magnetic susceptibility model in step S1402. The magnetic susceptibility image with high resolution has the matrix size set to 384×384×384, the dimension set to 32×32×32 (mm), and the voxel size set to 0.083×0.083×0.083 (mm). The coordinate origin of the magnetic susceptibility model is made coincided with the center (193, 193, 193) on the image. Arbitrary values may be set besides those described above. The calculation accuracy may be improved as the voxel size of the magnetic susceptibility image with high resolution becomes smaller.

The high resolution phase image is calculated from the high resolution magnetic susceptibility image using the relational expression between the phase and the magnetic susceptibility in step S1403. The relational expression between the phase and the magnetic susceptibility may be expressed by the following formula (1).

formula (1)

$$\phi(r) = \frac{\gamma B_0 \tau_{TE}}{4\pi} \int \chi(r') \frac{3\cos^2\alpha - 1}{|r' - r|^3} d^3 r' \quad (1)$$

Referring to the formula (1), $\varphi(r)$ denotes the phase (rad) at the position r in the image, $\gamma$ denotes the gyromagnetic ratio, $B_0$ denotes the static magnetic field intensity (T), the $\tau_{TE}$ denotes the TE(s), $\chi(r)$ denotes the magnetic susceptibility (ppm) at the position r in the image, $\alpha$ denotes the angle formed between the calculated static magnetic field direction (Z-direction) and the vector r'−r. The value $\gamma$ for the MRI is set to $267.4 \times 10^6$ $T^{-1}s^{-1}$. Assuming that Z components of the vectors r, r' are set to rz and r'z, cos $\alpha$ may be expressed by the formula (2).

formula (2)

$$\cos \alpha = |r'_z - r_z|/|r' - r| \quad (2)$$

In this embodiment, Fourier transformation is applied to the formula (1) to calculate the phase from the magnetic susceptibility using the relational expression (3) between the phase and the magnetic susceptibility on the Fourier space.

formula (3)

$$\Phi(k) = -\gamma B_0 \tau_{TE} \left( \frac{1}{3} - \frac{k_z^2}{k^2} \right) \cdot X(k) \quad (3)$$

Referring to the formula (3), $\Phi(k)$ denotes the phase at a position k on Fourier space, X(k) denotes the magnetic susceptibility at the position k on Fourier space with the formula of $k^2 = k_x^2 + k_y^2 + k_z^2$. Fourier transformation is applied to the magnetic susceptibility image with high resolution, which is substituted for X(k) in the formula (3). Inverse Fourier transformation is applied to the obtained $\Phi(k)$ to have the phase image with high resolution. There are various kinds of methods for calculating the phase image from the magnetic susceptibility image, for example, the method of providing the phase $\varphi(r)$ at left side by substituting the magnetic susceptibility $\chi(r')$ for the right side in the formula (1) and the like. It is possible to apply pseudo noise to the phase image with high resolution.

The phase image with low resolution is calculated from the phase image with high resolution in the case where the voxel size is set to dX (mm), dY (mm), and dZ (mm) in step S1404. In this embodiment, the complex image with high resolution is calculated from the magnitude image on the assumption that the phase image with high resolution and all the elements have the value of 1. The low frequency region around the center on the Fourier space of the calculated complex image is extracted. The phase component of the complex image is derived from the inverse Fourier transformation to calculate the phase image with low resolution, which reflects the partial volume effect. The phase image with low resolution has the image with the same size (32×32×32 (mm)) as that of the phase image with high resolution. The matrix size of the frequency region to be extracted is changed to have the phase image with the required voxel size (dX, dY, dZ). For example, assuming that dX=0.5, dY=2, and dZ=0.5, the region with 64×16×64 is extracted. There are various types of methods of calculating the low resolution phase image, for example, the method of carrying out the convolutional integration process of the high resolution complex image and the sinc function. Any other method may be used. It is possible to apply the pseudo noise to the low resolution phase image.

Then the magnetic susceptibility image is calculated from the low resolution phase image in step S1405. In the embodiment, the magnetic susceptibility image is calculated from the phase image by solving the formula (1) using the least squares method. Various kinds of method of calculating the magnetic susceptibility image have been proposed without limitation, for example, the method using the relational expression (3) between the phase and the magnetic susceptibility on the Fourier space.

In step S1406, the magnetic susceptibility estimation accuracy of the target tissue is calculated from the obtained magnetic susceptibility image. In this embodiment, the magnetic susceptibility of the pixel center of the low resolution magnetic susceptibility image is defined as an estimated magnetic susceptibility $\chi v'$, and an absolute value of the difference between the set magnetic susceptibility $\chi v$ and the estimated magnetic susceptibility $\chi v'$ is defined as the magnetic susceptibility estimation accuracy. That is, the magnetic susceptibility estimation accuracy may be derived from the following formula (4).

formula (4)

$$f(\theta 1, \theta 2, dX, dY, dZ) = |\chi v - \chi v'| \quad (4)$$

The term f($\theta$1, $\theta$2, dX, dY, dZ) denotes the magnetic susceptibility estimation accuracy obtained in the case where the vein running directions are set to $\theta$1, $\theta$2, and the voxel size is set to dX, dY, dZ. Any other method of calculating the magnetic susceptibility estimation accuracy may be employed, for example, by defining the ratio between $\chi v'$ and $\chi v$ ($\chi v'/\chi v$).

The calculation of f($\theta$1, $\theta$2, dX, dY, dZ) in the process from step S1402 to step S1406 is executed for each angle of the $\theta$1, $\theta$2 and each size of dX, dY, dZ in the limiting condition. It is possible to use the magnetic susceptibility estimation accuracy f($\theta$1, $\theta$2, dX, dY, dZ) preliminarily stored in the storage device 211. In such a case, the calculator simulation does not have to be executed.

Based on the magnetic susceptibility estimation accuracy f($\theta$1, $\theta$2, dX, dY, dZ) calculated in step S1303, an optimum voxel size is determined in step S1304. In this embodiment, an evaluation value g(dX, dY, dZ) of the magnetic susceptibility evaluation accuracy for each voxel size (dX, dY, dZ) is calculated from the f($\theta$1, $\theta$2, dX, dY, dZ), based on which the optimum voxel size is determined. This embodiment defines the minimum value of the magnetic susceptibility estimation accuracy in every running direction (θ1, θ2) as the evaluation value g(dX, dY, dZ) as expressed by the formula (5) for the purpose of calculating the voxel size which allows estimation of the magnetic susceptibility with high accuracy for the vein in any running direction. Furthermore, the embodiment determines the voxel size that maximizes the g(dX, dY, dZ) as the optimum voxel size.

formula (5)

$$g(dX,dY,dZ)=\min_{\theta 1,\theta 2}\{f(\theta 1,\theta 2,dX,dY,dZ)\} \quad (5)$$

The average value of the magnetic susceptibility estimation accuracy of all the target tissues, and the average value of the magnetic susceptibility estimation accuracy through weighting for each of the target tissues may be employed as the evaluation value in place of the minimum value of the magnetic susceptibility estimation accuracy as described above. Additionally, it is effective to set dispersion of the magnetic susceptibility estimation accuracy for all the target tissues as the evaluation value. In this case, the voxel size that minimizes the dispersion is determined as the optimum voxel size. It is also possible to use the definition as combined plural indexes, for example, minimum value, average value, dispersion and the like. Depending on definition of the evaluation value, the voxel size that minimizes the g(dX, dY, dZ) may be determined as the optimum voxel size. The definition of the evaluation value may be designated by the user, or the definition preliminarily stored in the storage device 211 may be used. The evaluation value g(dX, dY, dZ) which has been preliminarily stored in the storage device may be used. In such a case, the calculator simulation does not have to be executed.

In this embodiment, the voxel size calculated by the voxel size-calculating section 313 is set to have dX=0.5 mm, dY=1 mm, dZ=1 mm under the limiting condition set by the limiting condition-inputting section 312. At this time, the phase encoding direction is HF direction, the number of lead-out encodings is 512, the number of phase encodings is 256, the number of slice encodings is 32, and the slice thickness is 1 mm. The SNR rate of change is 100%, the in-plane resolution is 0.5 mm², and the imaging time is 8 minutes 12 seconds. In the case where the static magnetic field direction is in parallel with the imaging cross-section likewise the coronal cross-section in the horizontal magnetic field, the sagittal cross-section in the horizontal magnetic field, transverse section and the sagittal cross-section in the vertical magnetic field, the optimum voxel size is obtained when the resolution in the direction parallel to the static magnetic field direction as one of the two in-plane directions is 1 mm, the resolution in the vertical direction is 0.5 mm, and the resolution in the slice direction is 1 mm under the same limiting condition as that of the embodiment. In other words, the optimum voxel size may be obtained when the rate of the resolutions in the direction parallel to the static magnetic field and the direction vertical to the static magnetic field of the in-plane directions, and the slice direction becomes 2:1:2. Additionally, in the case where the static magnetic field is vertical to the imaging cross-section likewise the transverse section in the horizontal magnetic field and the coronal cross-section in the vertical magnetic field, the optimum voxel size may be obtained when each resolution in the two in-plane directions is 0.5 mm, and the resolution in the slice direction is 2 mm under the same limiting condition as that of the embodiment. That is, the optimum voxel size is obtained when the rate of the resolutions in the two directions of the imaging cross-section and the slice direction becomes 1:1:4.

The aforementioned results indicate that the anisotropic voxel size that increases the resolution in the static magnetic field direction and the slice direction becomes optimum for estimating the magnetic susceptibility with high accuracy irrespective of the vein in any running direction as the target tissue running omnidirectionally.

The optimality of the anisotropic voxel size for increasing the resolution both in the static magnetic field direction and the slice direction will be briefly described. The voxel size for increasing the resolution in the slice direction is made optimum by setting the lower limit of SNR, and the upper limits of the imaging time and the in-plane resolution with the limiting condition-inputting section. The resolution in the slice direction is increased, and the resolution in the phase encoding direction is decreased so as to ensure reduction in the imaging time and the in-plane resolution without deteriorating the SNR.

Figure 10:
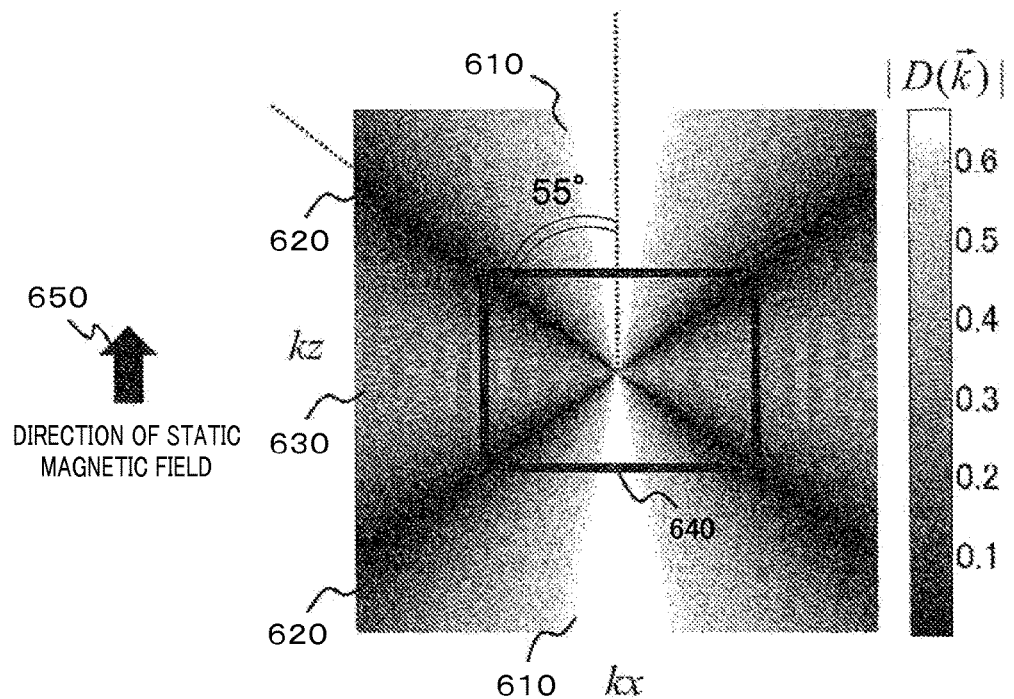
FIG. 10 represents the distribution of $D(k)=|\frac{1}{3}-k_z^2/k^2|$ on Fourier space.

The optimality of the voxel size that increases the resolution in the static magnetic field direction will be described using the relational expression (3) between the phase and the magnetic susceptibility on the Fourier space. Referring to $D(k)=|1/3-k_z^2/k^2|$ in the formula (3), it shows that the phase $D(k)$ at each position on the Fourier space is the product of the $D(k)$ and the magnetic susceptibility $X(k)$. FIG. 10 shows distribution of the absolute value $|D(k)|$ of the $D(k)$ on the Fourier space under the condition of $k_Y=0$, having $k_X$ set as x-axis and $k_Z$ set as y-axis. As FIG. 10 shows, the value of $|D(k)|$ becomes zero in a region 620 at the angle of approximately 55° with respect to the static magnetic field direction 650. For that reason, the magnetic susceptibility information in the region 620 at the angle of approximately 55° with respect to the static magnetic field direction is lost at the measured phase.

Meanwhile, upon application of Fourier transformation to the magnetic susceptibility model of the vein, there is a large value around the origin of the Fourier space (k=0) as the center in the region vertical to the vein running direction. For example, upon application of Fourier transformation to the magnetic susceptibility distribution of the vein running in the static magnetic field direction (z-direction), there is the large value in the plane with $k_z=0$ in the region 630. Then, the vein running at the angle of 35° with respect to the static magnetic field direction distributes around the region 620, and accordingly, most of the information is lost. Actually, reconstruction reduces the magnetic susceptibility estimation accuracy of the vein running around the area at 35° from the static magnetic field direction to the lowest value. In order to maximize the minimum value of the magnetic susceptibility estimation accuracy in all the running directions, it is necessary to set the voxel size that improves the magnetic susceptibility estimation accuracy of the vein running around the area at 35° from the static magnetic field direction. It is therefore necessary to cut the substantially broad region 640 in the one vertical to the static magnetic direction. At this time, the voxel size in the real space has the higher resolution in the direction parallel to the static magnetic field direction than in the direction vertical thereto. This clearly shows that the voxel size with higher resolution in the direction parallel to the static magnetic field becomes optimum for the purpose of improving the lowest magnetic susceptibility estimation accuracy of the vein.

In step S1304, the evaluation value g(dX, dY, dZ) is derived from averaging the estimation accuracy through weighting for each target tissues. For example, the evaluation value is derived from averaging the estimation accuracy by weighting the vein running in the X-direction to 100%, and the vein running in the other direction to 0% under the same condition as that of the embodiment to determine the optimum voxel shape. Then the resultant voxel size has dX=1 mm, dY=1 mm, dZ=0.5 mm. Likewise, the evaluation value is derived from averaging the estimation accuracy by weighting the vein running in the Y-direction to 100%, and the vein running in the other direction to 0% to determine the optimum voxel shape. The resultant voxel size has dX=0.5 mm, dY=2 mm, dZ=0.5 mm. The evaluation value is derived from averaging the estimation accuracy by weighting the vein running in the Z-direction to 100%, and the vein running in the other direction to 0% so as to determine the optimum voxel shape with the voxel size of dX=0.5 mm, dY=1 mm, dZ=1 mm.

Those results show that in the case of the vein as the tissue to be imaged running in the specific direction, the anisotropic voxel size that increases the resolution in the vein running direction and the slice direction (Y-direction) becomes optimum.

The voxel size-displaying section 314 displays the voxel size calculated by the voxel size-calculating section 313 on the voxel size display screen of the display device 210 in step S1204. In this embodiment, the imaging conditions such as the SNR rate of change, the in-plane resolution, and the imaging time are displayed simultaneously with the voxel size. The parameter in place of the voxel size, for example, the number of lead-out encodings, the number of phase encodings, the slice thickness, and the phase encoding direction may be displayed instead of the voxel size. The imaging condition does not have to be displayed, or the condition may be partially displayed.

FIG. 11 shows an example of the voxel size displaying screen. The calculated voxel size or the parameter in place of the voxel size is displayed on the voxel size-displaying section 710. The imaging condition corresponding to the calculated voxel size is displayed on an imaging condition-displaying section 720. FIG. 11 shows an example of the voxel size-displaying screen, which is not limited to the one shown in FIG. 11.

Various measurement parameters are set by the measurement parameter-setting section. Upon reception of the instruction to start imaging, the measuring unit 320 executes the measurement in step S1102. The measuring unit 320 instructs the sequencer 204 in accordance with the predetermined pulse sequence to acquire the echo signal, and places the signal in the space k. In response to the instruction, the sequencer 204 sends the command to the gradient magnetic field power source 205 and the high frequency magnetic field generator 206 so as to generate the gradient magnetic field and the high frequency magnetic field, respectively. The probe 207 receives the wave, and the receiver 208 receives the detected echo as the complex signal.

Figure 12:
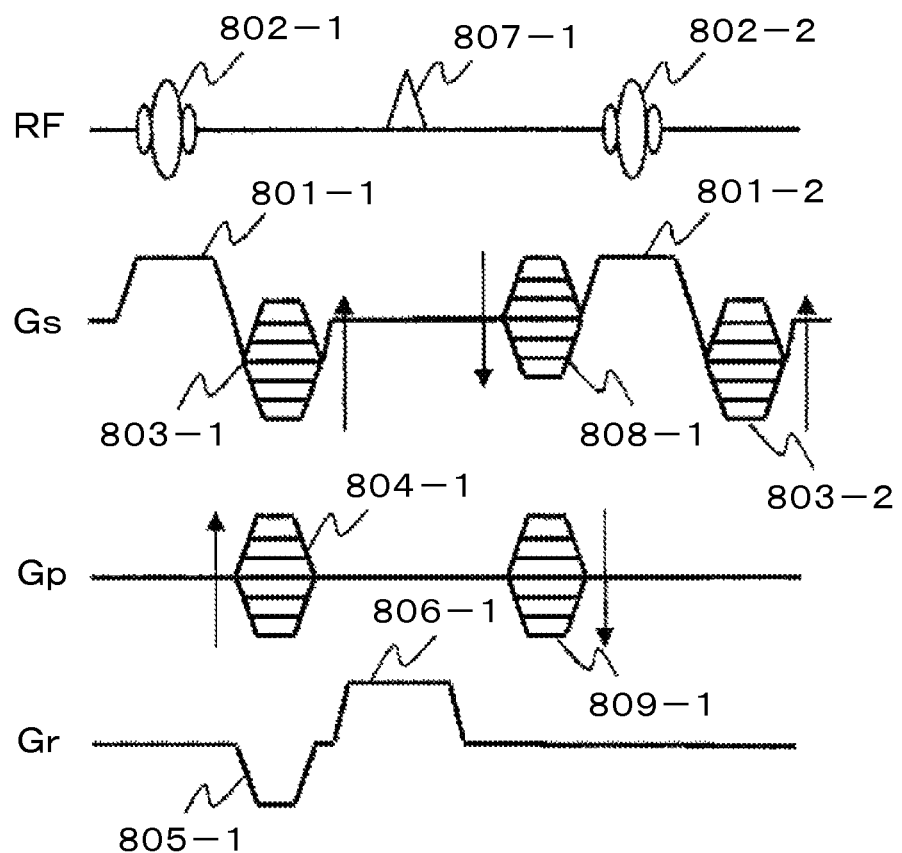
FIG. 12 is a pulse sequence diagram of RSSG (RF-Spoiled-Steady-State Acquisition with Rewound Gradient-Echo) sequence employed in the MRI apparatus according to the embodiment.

The embodiment employs the GrE pulse sequence as described above. The GrE pulse sequence employed in the embodiment will be described, taking the RSSG sequence as an example. FIG. 12 is a pulse sequence diagram of the RSSG sequence. Codes RF, Gs, Gp and Gr in the drawing denote the high frequency magnetic field, the slice gradient magnetic field, the phase encoding gradient magnetic field, and the lead-out gradient magnetic field, respectively. In the embodiment, the codes Gs, Gp and Gr correspond to the gradient magnetic fields in y-direction, z-direction and x-direction, respectively.

The RSSG sequence allows application of a slice gradient magnetic field pulse 801 and irradiation of a high frequency magnetic field (RF) pulse 802 so as to excite magnetization of the predetermined slice in the subject 203. Then a slice encoding gradient magnetic field pulse 803 and a phase encoding gradient magnetic field pulse 804 are applied for adding the positional information in the slice direction and the phase encoding direction to the magnetization phase. After applying a lead-out gradient magnetic field pulse 805 for dephasing, by which the nuclear magnetization phase in the pixel is dispersed, a single nuclear magnetic resonance signal (echo) 807 is measured while applying a lead-out gradient magnetic field pulse 806 for adding the positional information in the lead-out direction. Finally, a slice encoding gradient magnetic field pulse 808 and a phase encoding gradient magnetic field pulse 809 for rephasing are applied, which converge the nuclear magnetized phase that has been dephased by the slice encoding gradient magnetic field pulse 803 and the phase encoding gradient magnetic field pulse 804.

The measuring unit 320 repeats the aforementioned procedure while varying each intensity of the slice encoding gradient magnetic field pulses 803, 808 (the number of slice encodings ks) and the phase encoding gradient magnetic field pulses 804, 809 (the number of phase encodings kp), and the phase of the RF pulse 802, and measures the echo required to acquire the single image. The phase of the RF pulse 802 is increased by the angle of 117°. The number subsequent to the hyphen in FIG. 12 denotes the number of the repetition.

The respective measured echoes are arranged on the three-dimensional space k, taking kr, kp and ks as the coordinate axes. The single echo occupies the single line parallel to the kr-axis on the space k. The magnitude image derived from the RSSG sequence becomes a T1 (longitudinal relaxation time) high-contrast image by setting the short TE (time taken from irradiation of the RF pulse 802 to measurement of the echo 807), and becomes T2 high-contrast image which reflects the phase dispersion in the pixel by setting the long TE.

At the end of the measurement, the image reconstruction section 332 executes the image reconstruction process for reconstructing the image from the echo signal arranged in the space k in step S1103. At this time, the image reconstruction section 332 applies a three-dimensional inverse Fourier transformation to the echo (data) arranged on the space k so as to reconstruct the complex image having each pixel value expressed by the complex number.

In step S1104, the image transformation section 334 executes various kinds of image transformation process for the acquired complex image to be described later. The image transformation section 334 transforms the complex image acquired by the image reconstruction section 332 into the magnetic susceptibility image. The image transformation process according to the embodiment will be described in detail later.

The display processing unit 350 displays the acquired magnetic susceptibility image as a grayscale image on the display device 210 in step S1105. It is possible to display the information of a plurality of images which are integrated through such method as volume rendering.

Figure 13:
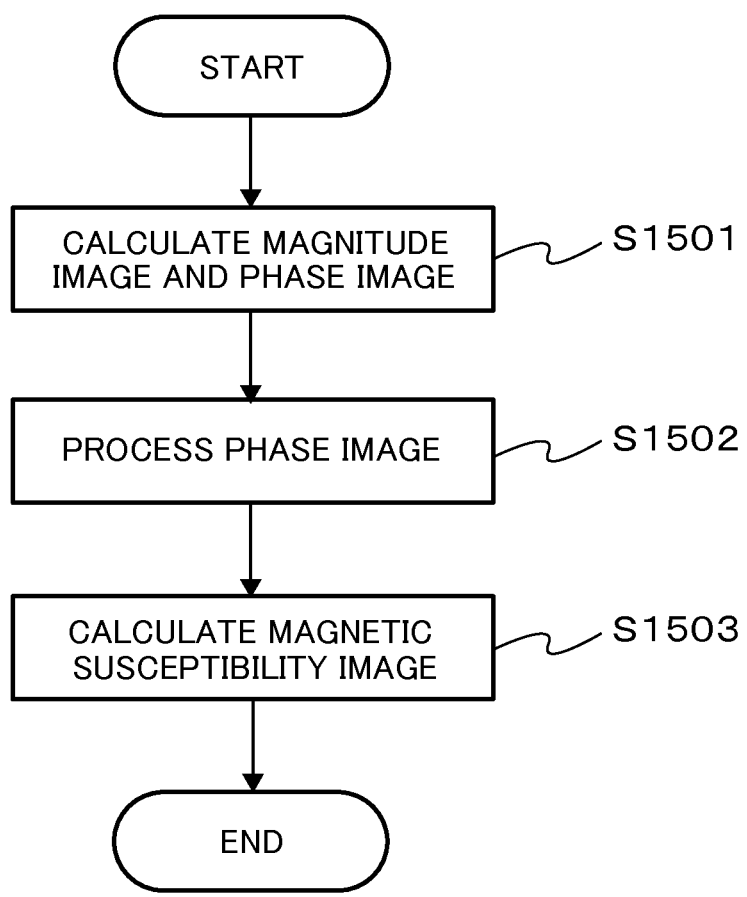
FIG. 13 is a flowchart of the image transforming process according to the present invention.

FIG. 13 is a flowchart of the image transformation process according to the embodiment. Upon start of the image transformation process by the image transformation section 334 according to the embodiment, in step S1501, the magnitude image and the phase image are generated from the complex image reconstructed by the image reconstruction section 332. The magnitude image and the phase image are generated from the magnitude component and the phase component of the complex number of each pixel of the complex image.

A luminance value S(i) of the magnitude image and a luminance value φ(i) of the phase image of the pixel i are calculated through formulae (6) and (7) using the luminance value of the complex image.

$$S(i)=|c(i)| \quad (6)$$

$$f(i)=arg\{c(i)\} \quad (7)$$

Figure 14:
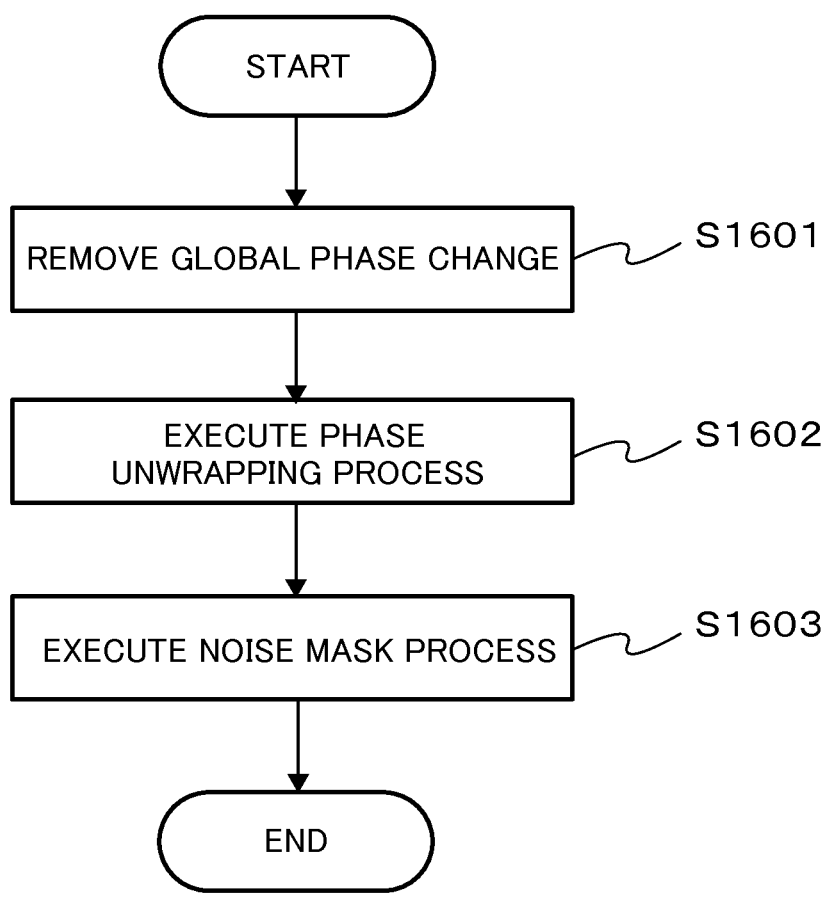
FIG. 14 is a flowchart of the phase imaging process according to the present invention.

The predetermined phase image processing is applied to the phase image in step S1502. In this embodiment, three types of phase image processing are executed. Those three types of phase image processing will be described referring to the process flow shown in FIG. 14. Use of the three types of processings is a mere example with no limitation. Those three types of processing may be partially omitted. The order of executing those process steps may be arbitrarily set.

The global phase change removing process for removing the global phase change from the phase image is executed in step S1601. The global phase change removing process is executed for calculating the local phase change owing to the change in the magnetic susceptibility between the tissues. The global phase change is caused by nonuniformity in the static magnetic field depending on the shape of the imaging site (for example, head part), corresponding to the low frequency component in the spatial frequency region (space k). In this embodiment, the low pass filtering process is applied to the imaged three-dimensional image (original image) by the two-dimensional image for calculating the low resolution image. Then the original image is subjected to complex division process with the low resolution image to remove the global phase change contained in the low resolution image from the original image.

There are various known methods for removing the global phase change. For example, besides the aforementioned methods, there is a method for extracting the global phase change by fitting the three-dimensional image with low order polynomial, and for subtracting the change from the original image. Any other method may be employed as the global phase change removing process according to the embodiment.

The phase unwrapping process for correcting the phase folding is executed in step S1602. In a part of the region of the phase image, the phase value in excess of the range from −π to π is folded therein. In this embodiment, the phase value folded in the range from −π to π is corrected with the area magnifying process as the known method.

A noise mask process is applied to the region of the phase image, which contains only the noise component (noise region) in step S1603. A mask image is generated using the magnitude image. The mask image is generated, having the pixel value in the region with the value smaller than a predetermined threshold value set to 0, and the pixel value in the other region set to 1. The thus generated mask image is multiplied by the phase image.

There are various known methods of the noise mask process. For example, it is possible to use the method of setting the pixel value of the mask image for the noise mask process in the air region to zero. In such a case, the boundary between the brain and air is detected, and the air region is extracted based on the detection result. Any other method may be used for executing the noise mask process in the embodiment.

The phase image processing does not have to be executed.

Figure 15:
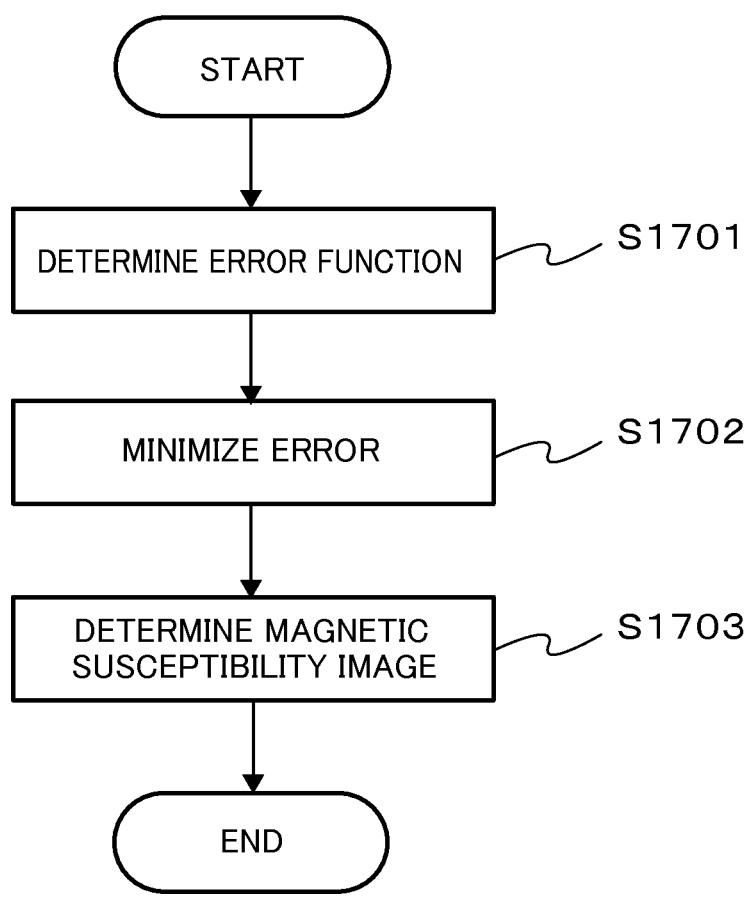
FIG. 15 is a flowchart of a magnetic susceptibility image calculation process according to the present invention.

The magnetic susceptibility image is generated from the phase image using the relationship between the phase and the magnetic susceptibility expressed by the formula (1) in step S1503. The process steps of generating the magnetic susceptibility image according to the embodiment will be described referring to the process flow shown in FIG. 15.

An error function indicating the difference between the calculated phase image and the magnetic susceptibility image candidate to be calculated is determined in step S1701. Then the magnetic susceptibility image candidate which minimizes the error function is determined in step S1702. The determined magnetic susceptibility image candidate is set as the magnetic susceptibility image in step S1703.

The error function is determined with the relationship between the phase Φ and the magnetic susceptibility χ which are expressed by the formula (1). As all the pixels in the phase image are subjected to the process, the formula (1) may be expressed by a determinant as indicated by a formula (8).

$$\Phi = C\chi \quad (8)$$

where Φ denotes the column vector of the phase image with the size corresponding to the number N of all the pixels, χ denotes the column vector of the magnetic susceptibility image candidate, and C denotes the matrix with the size of N×N corresponding to the convolution arithmetic operation to the χ.

In this embodiment, the magnetic susceptibility image is acquired from the formula (8) through L1 norm minimizing method. The magnetic susceptibility image candidate for minimization is determined with the error function e(χ) expressed by the following formula (9).

formula (9)

$$e(\chi) = \|W \cdot (C_\chi - \delta)\|^2 + \lambda \sum_{i=1}^{N} |\chi_i| \quad (9)$$

The code W denotes the column vector with the size N as the coefficient vector for weighting the error in each pixel. The code "·" denotes multiplication for each vector element, //*// denotes the norm of "*", and λ denotes the arbitrary constant.

In the embodiment, the pixel value of the magnitude image is used for the coefficient vector W in the formula (8). Specifically, the value W(i) of the coefficient vector for the arbitrary pixel i (i=1, 2, . . . , N) is derived from the following formula (10).

$$W(i)=S(i)/S_{max} \quad (10)$$

where S(i) denotes the absolute value (pixel value of the magnitude image) in the pixel i, and the $S_{max}$ denotes the maximum value of the magnitude image among all the pixel values. As the SNR of the image deteriorates, dispersion of the phase owing to noise is increased. The pixel value of the magnitude image in proportional to the SNR is used as the coefficient vector W so as to lessen contribution of the pixel with larger dispersion in the phase to the error function, and to improve accuracy in the magnetic susceptibility image x to be calculated.

The error function to be calculated may be expressed by the formula other than those (9) and (10). For example, the coefficient vector W may be derived from raising the magnitude image to n-th power (n: positive real number), or setting only the pixel value in the region where the magnetic susceptibility image is required to be acquired to 1, and setting the other pixel value to 0. The function type of the error function e(χ) of the formula (9) may be modified. For example, it is possible to use various known function types, for example, by adding the regularization term called L2 norm, or the more generally employed regularization term called Lp norm (p>0) to the formula (9).

In the embodiment, the error calculated based on the error function e($\chi$) is minimized by executing repeated operations through the conjugate gradient method. It is possible to use any one of various known methods for minimizing the error function, for example, the steepest descent method or the like.

Besides the aforementioned method for minimizing the error function, other method may be used for calculating the magnetic susceptibility image from the phase image. For example, Fourier transformation is applied to the formula (7) to acquire the magnetic susceptibility image on the Fourier space. The inverse Fourier transformation is applied to the acquired image so that the magnetic susceptibility image on the real space may be obtained.

It is also possible to calculate the single magnetic susceptibility image from a plurality of complex images acquired by the measurement a plurality of times while variously changing the angle of the imaging part (for example, head part) with respect to the fixed static magnetic field direction. Change in the angle of the imaging part (for example, head part) with respect to the fixed static magnetic field direction corresponds to various change in the static magnetic field direction applied to the magnetic susceptibility distribution of the imaging tissue (for example, brain tissue). Therefore, the measurement allows acquisition of a plurality of phase images to which the differently directed static magnetic fields are applied. Calculation of the magnetic susceptibility image from those phase images ensures to improve the solution accuracy higher than the one derived from the single phase image. There are various types of known methods of calculating the magnetic susceptibility image as described above, any one of which may be employed.

The magnetic susceptibility image according to the embodiment has the voxel size set to allow estimation of the magnetic susceptibility with high accuracy irrespective of the vein running in any direction. Accordingly, the contrast of the vein in the magnetic susceptibility image is not lessened irrespective of the running direction of the vein. For verification of this, a comparison is made between the magnetic susceptibility image obtained when setting the voxel size normally used for the magnetic susceptibility high-contrast image, and the magnetic susceptibility image obtained when setting the voxel size calculated in the embodiment on the coronal cross-section of the horizontal magnetic field.

Figure 16A:
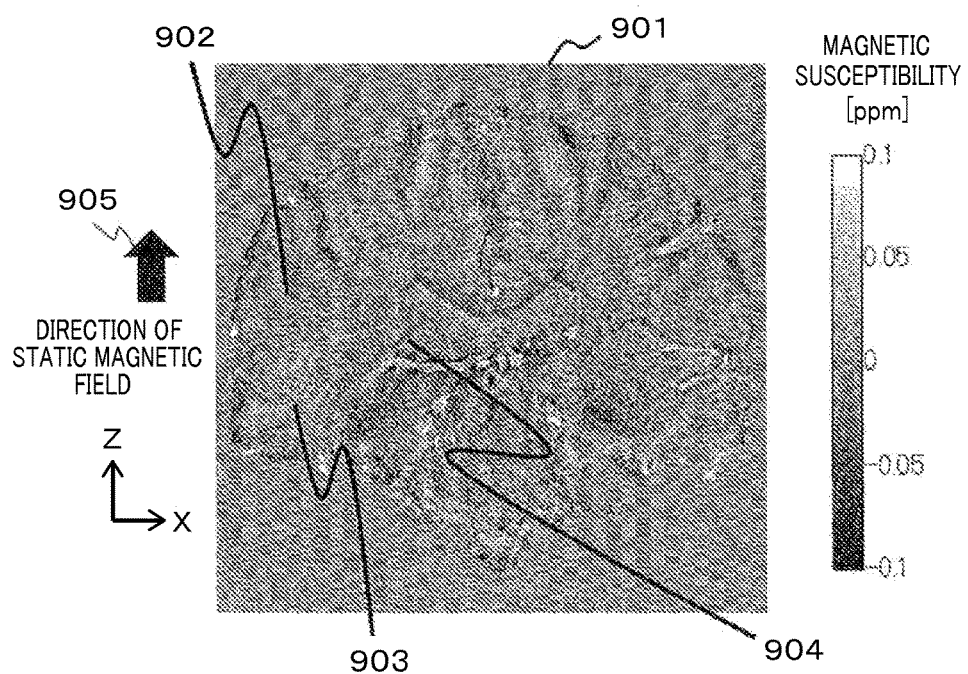
FIG. 16A represents a magnetic susceptibility image of the coronal section with the pixel size of (dx, dy, dz)=(0.5, 2, 0.5).
Figure 16B:
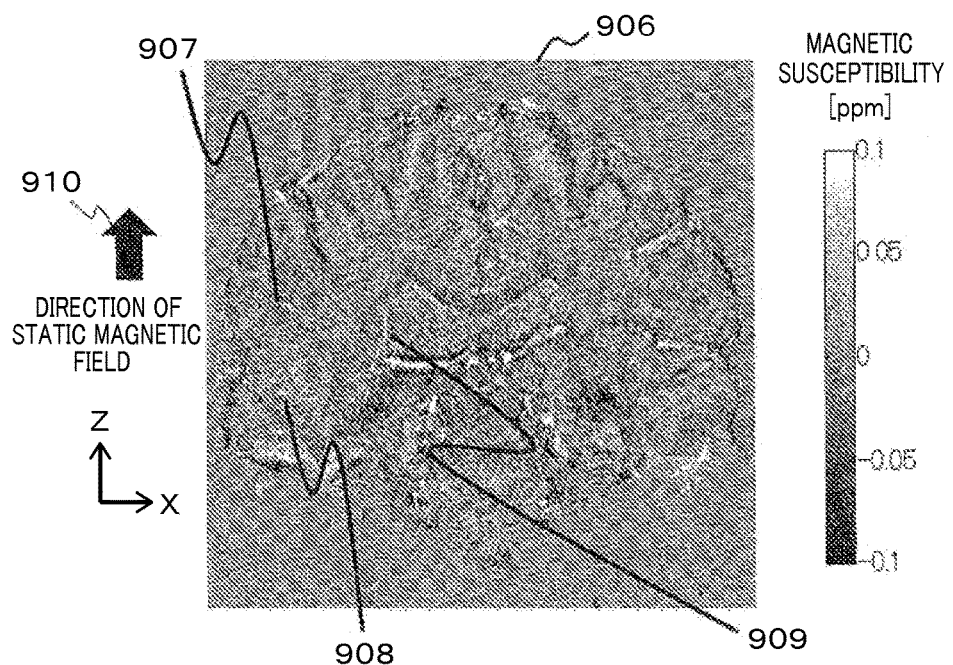
FIG. 16B represents a magnetic susceptibility image of the coronal section with the pixel size of (dx, dy, dz)=(0.5, 1, 1).

FIGS. 16A and 16B show magnetic susceptibility images on the coronal cross-sections of the horizontal magnetic field. FIG. 16A shows the magnetic susceptibility image with the voxel size ((dx, dy, dz)=(0.5, 2, 0.5)) used for the normal magnetic susceptibility high-contrast image. FIG. 16B shows the magnetic susceptibility image of the voxel size ((dx, dy, dz)=(0.5, 1, 1)) calculated in the embodiment. The veins 902, 903, 904 shown in FIG. 16A are compared with the veins 907, 908, 909 shown in FIG. 16B. The magnetic susceptibility image with the voxel size usually employed for the magnetic susceptibility high-contrast image (FIG. 15A) fails to visualize the veins 902, 903, 904. On the contrary, the magnetic susceptibility image with the voxel size calculated in the embodiment (FIG. 15B) visualizes the veins 907 and 908 running in the direction vertical to the static magnetic field direction 910, and the vein 909 running in the direction parallel to the static magnetic field direction.

Figure 17A:
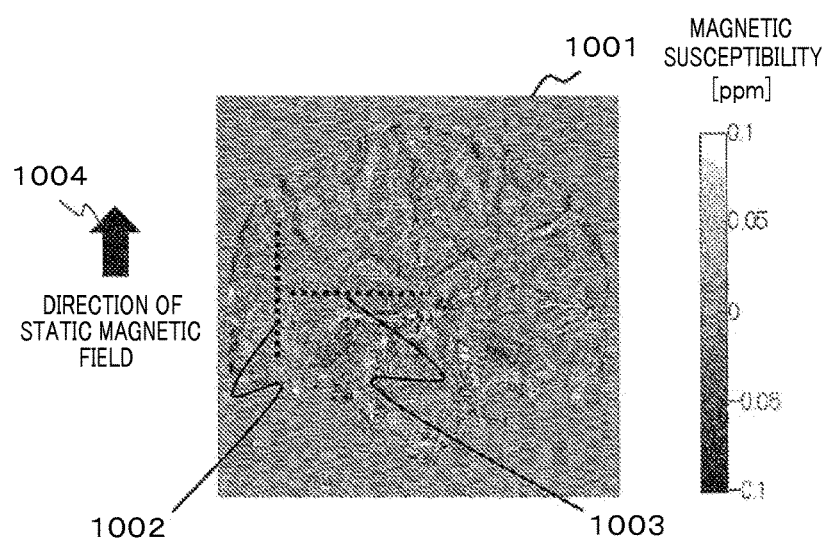
FIG. 17A represents a magnetic susceptibility image of the coronal section with the pixel size of (dx, dy, dz)=(0.5, 2, 0.5).
Figure 17B:
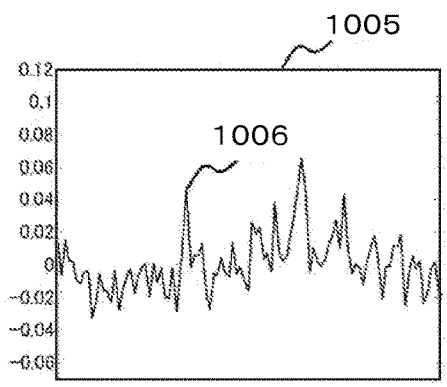
FIG. 17B represents a luminance profile of the image shown in FIG. 17A.
Figure 17C:
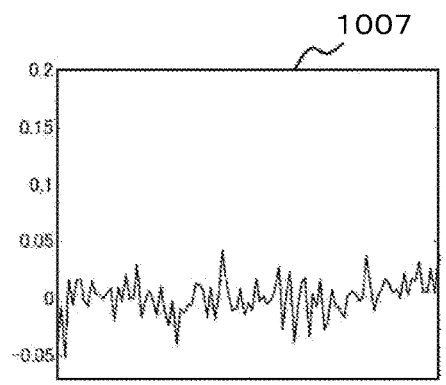
FIG. 17C represents a luminance profile of the image shown in FIG. 17A.
Figure 18A:
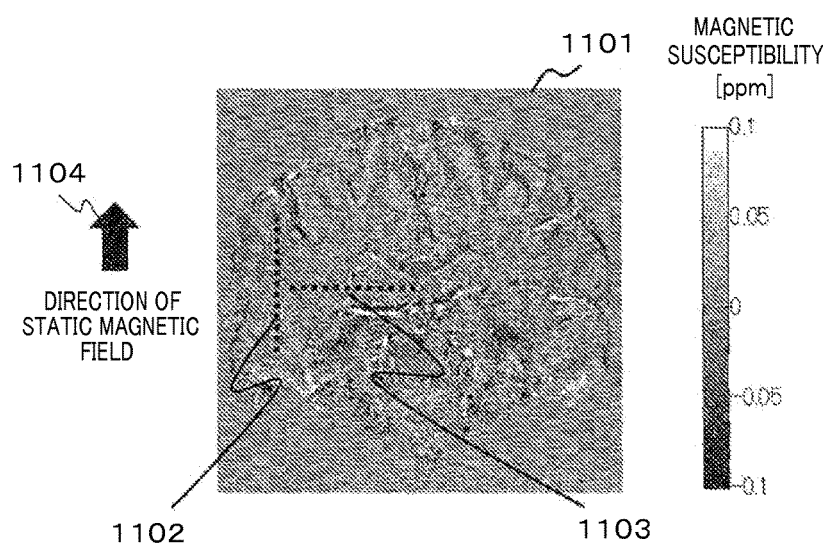
FIG. 18A represents a magnetic susceptibility image of the coronal section with the pixel size of (dx, dy, dz)=(0.5, 1, 1).
Figure 18B:
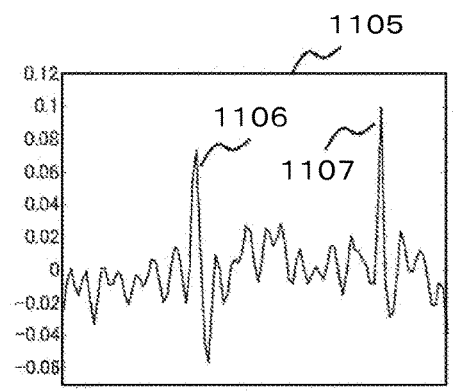
FIG. 18B represents a luminance profile of the image shown in FIG. 18A.
Figure 18C:
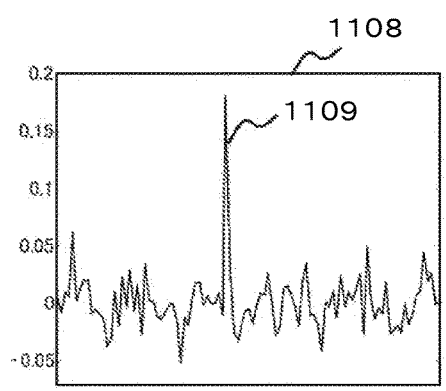
FIG. 18C represents a luminance profile of the image shown in FIG. 18A.

Those results will be examined in detail using the luminance profile. FIG. 17A represents the magnetic susceptibility image on the coronal cross-section of the horizontal magnetic field with the size (dx, dy, dz)=(0.5, 2, 0.5). FIG. 17B represents the luminance profile of a line segment 1002 of an image 1001. FIG. 17C represents the luminance profile of a line segment 1003 of the image 1001. FIG. 18A represents the magnetic susceptibility image on the coronal cross-section of the horizontal magnetic field with the size (dx, dy, dz)=(0.5, 1, 1). FIG. 18B represents the luminance profile of a line segment 1102 of an image 1101. FIG. 18C represents the luminance profile of a line segment 1103 of the image 1101. Referring to FIG. 17B, the vein 1006 is expressed by the luminance profile 1005. However, the other vein is not expressed by the profiles 1005 and 1006. Meanwhile, FIGS. 18B and 18C show that the veins 1106 and 1107 are clearly expressed by the luminance profile 1105, and the vein 1109 is clearly expressed by the luminance profile 1108, respectively.

The aforementioned results show that the contrast of the vein of the magnetic susceptibility image according to the embodiment is not lowered irrespective of the running direction of the vein because of the voxel size set to allow estimation of the magnetic susceptibility with high accuracy with respect to the vein running in any direction.

In the embodiment, the coronal cross-section of the horizontal magnetic field MRI has been described. However, the apparatus and the imaging cross-section are not limited to those described above. The use of the vertical magnetic field type MRI and any other apparatus ensures to execute the similar process to provide the similar effects. The similar process may be applied to the arbitrary imaging cross-section, for example, coronal cross-section, sagittal cross-section, and oblique cross-section to provide the similar effects.

The magnetic susceptibility image is subjected to the image processing to generate the image with contrast different from that of the magnetic susceptibility image. Such image may be displayed on the display device 210. For example, the highlight mask that highlights the magnetic susceptibility difference is derived from the magnetic susceptibility image. It may be multiplied by the magnitude image so as to be displayed.

In this embodiment, the estimated magnetic susceptibility $\chi v'$ is obtained from the magnetic susceptibility $\chi v$ set in the voxel size-calculating section 313 for the purpose of calculating the voxel size by which the magnetic susceptibility is estimated with high accuracy. This may be applied to the other object. For example, it is applicable to acquisition of the accurate magnetic susceptibility of the target tissue. Generally, the accurate magnetic susceptibility of the tissue smaller than the voxel size cannot be obtained as the magnetic susceptibility estimation accuracy is lessened by the partial volume effect of the phase image. For this, the rate of change of the calculated magnetic susceptibility of the target tissue from the true magnetic susceptibility is preliminarily calculated. The resultant value is used as the correction value to correct the calculated magnetic susceptibility to ensure the accurate magnetic susceptibility. Specifically, if the vein is the target tissue, the vein shape is assumed to have the column shape (diameter D, length L, angles of running direction $\theta 1, \theta 2$) so as to calculate the ratio between the set magnetic susceptibility $\chi v$ and the estimated magnetic susceptibility $\chi v'$, that is, $\chi v/\chi v'$ with respect to the voxel size (dX, dY, dZ) used for the measurement. The resultant ratio is set to the rate of change to be multiplied by the calculated magnetic susceptibility, thus providing the accurate magnetic susceptibility. Besides the vein, the tissue with arbitrary shape such as the microbleed may be set as the target tissue.

In the embodiment, the phase image with low resolution is calculated by the voxel size-calculating section 313 for the purpose of calculating the voxel size by which the magnetic susceptibility is estimated with high accuracy. This can be applied to the other object. For example, it may be applied to calculation of the voxel size for increasing the contrast of the phase image of the target tissue. Specifically, the voxel size which maximizes the contrast of the target tissue in the low resolution phase image is calculated in the limiting condition range. The calculated voxel size used for the measurement ensures to intensify the contrast of the target tissue in the measured phase image. It is possible to aim at acquisition of the accurate phase of the target tissue. Specifically, if the vein is set as the target tissue, the vein is assumed to have the column shape (diameter D, length L, angle in the running direction θ1, θ2) so as to calculate the ratio between the phase φv of the target tissue in the high resolution phase image and the phase φv' of the target tissue in the low resolution phase image with respect to the voxel size (dX, dY, dZ) used for the measurement, that is, the ratio of φv/φv'. The ratio is set as the rate of change. It is multiplied by the phase of the target tissue in the measured phase image to provide the accurate phase. Besides the vein, the tissue with arbitrary shape, for example, microbleed may be set as the target tissue.

This embodiment uses the RSSG sequence as one of Cartesian imaging for obtaining data in parallel with the coordinate axis of the space k. However, it is possible to use the arbitrary sequence to obtain the data in arbitrary region of the space k. For example, the non-Cartesian imaging may be used, for example, radial scan for rotatably obtaining the data in the space k. It is also possible to execute the imaging process a plurality of times for obtaining individual data in the respective regions of the space k. The data derived from integrating those obtained may be used.

In the embodiment, each function of the image reconstruction unit, the image transformation unit, and the display processing unit has been described, taking the case where it is realized in the calculator of the MRI apparatus as an example. However, the functions are not limited to those described above. At least one of those units may be configured on the information processing device, which is separated from the MRI apparatus capable of transmitting and receiving the data to and from the calculator 209 of the MRI apparatus.

What is claimed is:

1. A magnetic resonance imaging apparatus comprising:
a static magnetic field application unit that applies a static magnetic field to a subject;
a gradient magnetic field application unit that applies a gradient magnetic field to the subject;
a high frequency magnetic field pulse irradiation unit that irradiates the subject with a high frequency magnetic field pulse;
a receiving unit that receives a nuclear magnetic resonance signal from the subject; and
a calculation unit that performs an operation with respect to the received nuclear magnetic resonance signal by controlling the gradient magnetic field and the high frequency magnetic field pulse,
wherein the calculation unit includes:
a measurement parameter setting unit that sets a measurement parameter which determines intensity and timing of a high frequency magnetic field and the gradient magnetic field,
a measuring unit that applies the high frequency magnetic field and the gradient magnetic field to the subject placed in the static magnetic field in accordance with the measurement parameter in order to detect the nuclear magnetic resonance signal generated from the subject as a complex signal,
an operation unit that performs an operation with respect to the complex signal in order to generate an image, and
a display processing unit that displays the generated image on a display device, wherein the measurement parameter setting unit includes:
a basic parameter inputting unit that sets an imaging parameter and an imaging cross-section,
a limiting condition inputting unit that sets a limiting condition that limits a voxel size setting,
a voxel size calculating unit that sets a voxel size in accordance with the limiting condition, and
a voxel size displaying unit that displays the set voxel size to a user, and
wherein the voxel size calculating unit includes:
a magnetic susceptibility estimation accuracy calculating unit that calculates a magnetic susceptibility estimation accuracy of a target tissue by:
setting a magnetic susceptibility model of the target tissue,
calculating a high resolution magnetic susceptibility image from the set magnetic susceptibility model,
calculating a high resolution phase image from the calculated high resolution magnetic susceptibility image,
calculating a low resolution phase image from the calculated high resolution phase image,
calculating a low resolution magnetic susceptibility image from the calculated low resolution phase image, and
calculating the magnetic susceptibility estimation accuracy from the calculated low resolution magnetic susceptibility image, and
a voxel size determination unit that determines the voxel size in accordance with the magnetic susceptibility estimation accuracy provided by the magnetic susceptibility estimation accuracy calculating unit.

2. The magnetic resonance imaging apparatus according to claim 1, wherein the limiting condition inputting unit includes a target tissue setting unit that sets a shape of the target tissue to be imaged.

3. The magnetic resonance imaging apparatus according to claim 1, wherein the limiting condition inputting unit includes an imaging condition setting unit that sets an SNR, an in-plane resolution and an imaging time.

4. The magnetic resonance imaging apparatus according to claim 1, wherein the voxel size determination unit further determines the voxel size that minimizes dispersion of the magnetic susceptibility estimation accuracy with respect to each of the target tissues under the limiting condition.

5. The magnetic resonance imaging apparatus according to claim 1, wherein the voxel size calculating unit includes a static magnetic field direction calculating unit that calculates a magnetic field direction of the static magnetic field with respect to the imaging cross-section.

6. The magnetic resonance imaging apparatus according to claim 1, wherein the magnetic susceptibility estimation accuracy calculating unit calculates the magnetic susceptibility estimation accuracy of the target tissue with respect to a voxel size through a calculated simulation.

7. The magnetic resonance imaging apparatus according to claim 6, wherein the magnetic susceptibility estimation accuracy calculating unit includes:
   a magnetic susceptibility model setting unit that sets the magnetic susceptibility model of the target tissue,
   a high resolution magnetic susceptibility image calculating unit that calculates the high resolution magnetic susceptibility image from the set magnetic susceptibility model,
   a high resolution phase image calculating unit that calculates the high resolution phase image from the calculated high resolution magnetic susceptibility image,
   a low resolution phase image calculating unit that calculates the low resolution phase image from the calculated high resolution phase image, and
   a low resolution magnetic susceptibility image calculating unit that calculates the low resolution magnetic susceptibility image from the calculated low resolution phase image.

8. The magnetic resonance imaging apparatus according to claim 1, wherein the magnetic susceptibility estimation accuracy calculating unit uses a preliminarily stored magnetic susceptibility estimation accuracy of the target tissue with respect to the determined voxel size.

9. The magnetic resonance imaging apparatus according to claim 1, wherein the voxel size determination unit further determines the voxel size which maximizes a minimum value among values of the magnetic susceptibility estimation accuracy for all target tissues under the limiting condition.

10. The magnetic resonance imaging apparatus according to claim 9, wherein the voxel size determination unit further determines an anisotropic voxel having a resolution in a slice direction parallel to the static magnetic field in a slice plane, which is larger than the resolution in a direction vertical to the static magnetic field in the slice plane as the voxel size.

11. The magnetic resonance imaging apparatus according to claim 10, wherein when the imaging cross-section is a coronal cross-section, sagittal cross-section of the horizontal magnetic field type MRI, a transverse section, or a sagittal cross-section of a vertical magnetic field type MRI, the voxel size determination unit further determines the voxel size with a rate of the voxel sizes in an in-plane direction parallel to the static magnetic field direction, an in-plane direction vertical to the static magnetic field direction and the slice direction set to 2:1:2.

12. The magnetic resonance imaging apparatus according to claim 10, wherein when the imaging cross-section is a transverse section of a horizontal magnetic field type MRI, or a coronal cross-section of a vertical magnetic field type MRI, the voxel size determination unit further determines the voxel size with a rate of the voxel sizes in two directions in the imaging cross-section, and the slice direction set to 1:1:4.

13. The magnetic resonance imaging apparatus according to claim 1, wherein the voxel size determination unit further determines the voxel size that maximizes an evaluation value obtained by averaging the magnetic susceptibility estimation accuracy with respect to each of the target tissues under the limiting condition.

14. The magnetic resonance imaging apparatus according to claim 1, wherein the voxel size determination unit further determines the voxel size that maximizes an evaluation value among those of the magnetic susceptibility estimation accuracy with respect to all the target tissues, which is obtained by averaging the estimation accuracy through a weighting of each of the target tissues under the limiting condition.

* * * * *